United States Patent
Ho et al.

(10) Patent No.: US 9,416,190 B2
(45) Date of Patent: Aug. 16, 2016

(54) MESOTHELIN ANTIBODIES AND METHODS FOR ELICITING POTENT ANTITUMOR ACTIVITY

(71) Applicant: The United States of America, as represented by the Secretary, Department of Health and Human Services, Washington, DC (US)

(72) Inventors: Mitchell Ho, Urbana, MD (US); Ira H. Pastan, Potomac, MD (US); Dimiter S. Dimitrov, Frederick, MD (US); Zhewei Tang, Rockville, MD (US); Mingqian Feng, Rockville, MD (US); Wei Gao, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/428,771

(22) PCT Filed: Sep. 16, 2013

(86) PCT No.: PCT/US2013/059883
§ 371 (c)(1),
(2) Date: Mar. 17, 2015

(87) PCT Pub. No.: WO2014/052064
PCT Pub. Date: Apr. 3, 2014

(65) Prior Publication Data
US 2015/0274836 A1  Oct. 1, 2015

Related U.S. Application Data

(60) Provisional application No. 61/706,396, filed on Sep. 27, 2012.

(51) Int. Cl.
| C07K 16/30 | (2006.01) |
| A61K 39/395 | (2006.01) |
| G01N 33/53 | (2006.01) |
| G01N 33/574 | (2006.01) |
| A61K 39/00 | (2006.01) |

(52) U.S. Cl.
CPC .......... *C07K 16/30* (2013.01); *G01N 33/57492* (2013.01); *A61K 2039/505* (2013.01); *C07K 2317/21* (2013.01); *C07K 2317/30* (2013.01); *C07K 2317/52* (2013.01); *C07K 2317/56* (2013.01); *C07K 2317/569* (2013.01); *C07K 2317/73* (2013.01); *C07K 2317/732* (2013.01); *C07K 2317/734* (2013.01); *C07K 2319/00* (2013.01); *G01N 2333/705* (2013.01)

(58) Field of Classification Search
CPC .......... C07K 16/00–16/468; A61K 47/48484; A61K 47/48561; A61K 47/48569; G01N 33/57492
See application file for complete search history.

(56) References Cited

U.S. PATENT DOCUMENTS

| 8,268,970 | B2 * | 9/2012 | Terrett | A61K 39/39558 530/387.1 |
| 8,357,783 | B2 * | 1/2013 | Dimitrov | C07K 16/30 424/130.1 |
| 8,460,660 | B2 * | 6/2013 | Ho | C07K 16/30 424/130.1 |
| 9,084,829 | B2 * | 7/2015 | Kahnert | A61K 47/48569 |
| 2015/0252118 | A1 * | 9/2015 | Ho | A61K 47/48561 424/156.1 |

FOREIGN PATENT DOCUMENTS

| WO | WO 2007/016150 | 2/2007 |
| WO | WO 2010/111282 | 9/2010 |

OTHER PUBLICATIONS

Feng et al., "A Novel Human Monoclonal Antibody that Binds with High Affinity to Mesothelin-Expressing Cells and Kills Them by Antibody-Dependent Cell-Mediated Cytotoxicity," *Mol. Cancer Ther.*, vol. 8:1113-1118, 2009.
Ho et al., "A Novel High-Affinity Human Monoclonal Antibody to Mesothelin," *Int. J. Cancer*, vol. 128:2020-2030, 2011.
Tang et al., "A Human Single-Domain Antibody Elicits Potent Antitumor Activity by Targeting an Epitope in Mesothelin Close to the Cancer Cell Surface," *Mol. Cancer Ther.*, vol. 12:416-426, 2013.

* cited by examiner

*Primary Examiner* — Jessica H Roark
(74) *Attorney, Agent, or Firm* — Klarquist Sparkman, LLP

(57) ABSTRACT

Described herein is the use of phage display antibody engineering technology and synthetic peptide screening to identify SD1 and SD2, human single-domain antibodies to mesothelin. SD1 recognizes a conformational epitope at the C-terminal end (residues 539-588) of human mesothelin close to the cell surface. SD2 binds full-length mesothelin. To investigate SD1 as a potential therapeutic agent, a recombinant human Fc (SD1-hFc) fusion protein was generated. The SD1-hFc protein exhibits strong complement-dependent cytotoxicity (CDC), in addition to antibody-dependent cellular cytotoxicity (ADCC), against mesothelin-expressing tumor cells. Furthermore, the SD1-hFc protein causes significant tumor growth inhibition of tumor xenografts in nude mice. SD1 and SD2 are the first human single-domain antibodies targeting mesothelin-expressing tumors.

28 Claims, 11 Drawing Sheets

FIG. 1A

Mesothelin

I  II  III

SS1P/MORAb-009/HN1 binding

SD1 binding

Mesothelin expression ( fluorescence intensity)

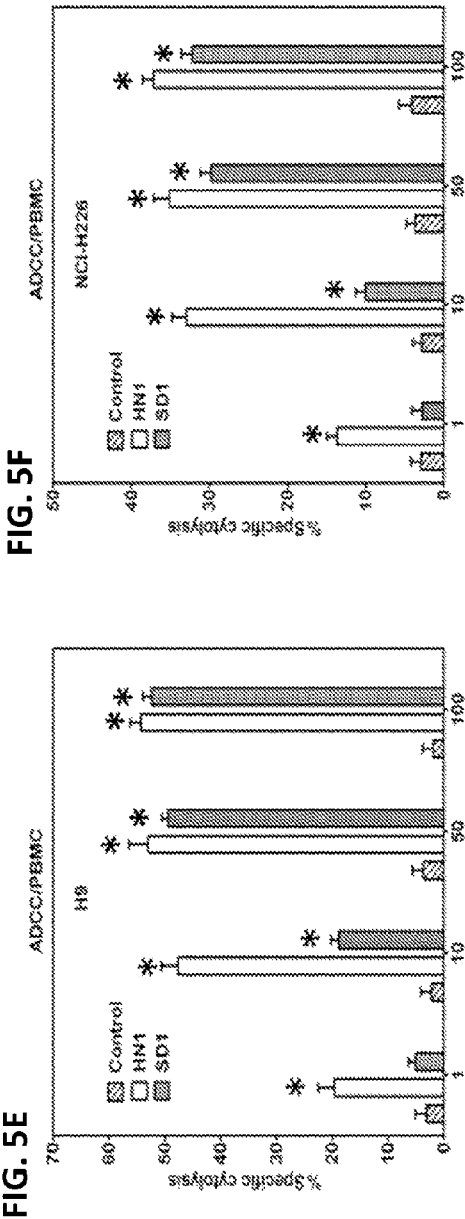
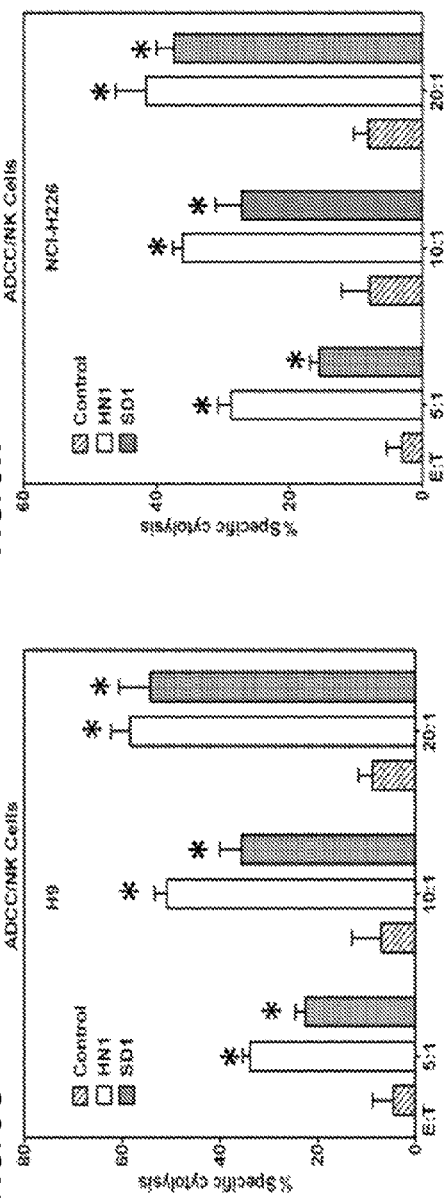
FIG. 5E
FIG. 5F
FIG. 5G
FIG. 5H

MESOTHELIN ANTIBODIES AND METHODS FOR ELICITING POTENT ANTITUMOR ACTIVITY

CROSS REFERENCE TO RELATED APPLICATIONS

This is the U.S. National Stage of International Application No. PCT/US2013/059883, filed Sep. 16, 2013, published in English under PCT Article 21(2), which claims the benefit of U.S. Provisional Application No. 61/706,396, filed Sep. 27, 2012, which is herein incorporated by reference in its entirety.

FIELD

This disclosure concerns monoclonal antibodies, such as single-domain monoclonal antibodies, specific for mesothelin. This disclosure further concerns the use of such antibodies, such as for the detection and treatment of cancer.

BACKGROUND

Mesothelin has been suggested as a therapeutic target because it is highly expressed in malignant mesotheliomas (Chang et al., *Cancer Res* 52:181-186, 1992; Chang and Pastan, *Proc Natl Acad Sci USA* 93:136-140, 1996) and other solid tumors, such as stomach cancer, squamous cell carcinomas, prostate cancer, pancreatic cancer, lung cancer, cholangiocarcinoma, breast cancer and ovarian cancer (Hassan et al., *Clin. Cancer Res.* 10:3937-3942, 2004; McGuire et al., *N. Engl. J. Med.* 334:1-6, 1996; Argani et al., *Clin. Cancer Res.* 7:3862-3868, 2001; Hassan et al., *Appl. Immunohistochem. Mol. Morphol.* 13:243-247, 2005; Li et al., *Mol. Cancer Ther.* 7:286-296, 2008; Yu et al., *J Cancer* 1:141-1749, 2010; Tchou et al., *Breast Cancer Res Treat* 133(2):799-804, 2012; U.S. Pat. No. 7,081,518).

The mesothelin (MSLN) gene encodes a ~70 kDa precursor protein that is processed to a ~30 kDa N-terminal protein and a ~40 kDa C-terminal membrane-bound mature mesothelin (Hassan and Ho, *Eur J Cancer* 44:46-53, 2008). Over the last two decades, a number of anti-mesothelin monoclonal antibodies (mAbs) have been developed, including SS1P immunotoxin and MORAb-009 (also known as amatuximab), which are currently being evaluated in clinical trials for mesothelioma and other cancers (Hassan and Ho, *Eur J Cancer* 44:46-53, 2008; Ho, Biodrugs 25:275-284, 2011). SS1P is a recombinant immunotoxin consisting of a murine anti-mesothelin Fv fused to a truncated *Pseudomonas* exotoxin that mediates cell killing (Pastan and Hassan, *Nat Rev Cancer* 6:559-565, 2006). A clinical trial of SS1P in combination with chemotherapy is currently ongoing. MORAb-009, a chimeric (mouse/human) antibody based on the murine SS1 Fv, elicits antibody-dependent cell-mediated cytotoxicity (ADCC) on mesothelin-bearing tumor cells (Hassan et al., *Cancer Immun* 7:20, 2007).

Investigators at the U.S. National Cancer Institute (NCI) recently generated two fully human mAbs (m912 and HN1) that recognize mesothelin (Feng et al., *Mol Cancer Ther* 8:1113-1118, 2009; Ho et al., *Int J Cancer* 128:2020-2030, 2011). The HN1 human Fv was isolated from a phage display library and a fully human IgG was generated. An HN1 immunotoxin was also generated by fusing the HN1 Fv to a truncated *Pseudomonas* exotoxin A (PE38) (Ho et al., *Int J Cancer* 128:2020-2030, 2011). HN1 IgG binds to cell surface-associated mesothelin and kills cancer cells with very strong ADCC. The HN1 human antibody recognizes a conformational epitope overlapping the SS1 site in mesothelin, indicating that HN1 can be developed as a fully human version of SS1-based mAbs (such as MORAb-009). Despite the number of known mesothelin mAbs available, none have shown complement-dependent cytotoxicity (CDC) against tumor cells. Therefore, current mesothelin-targeted therapy is hampered by the lack of anti-mesothelin mAbs with potent CDC.

CDC is an important mechanism of cell killing for therapeutic antibodies (Weiner et al., *Nat Rev Immunol* 10:317-327, 2010). The first approved mAb for cancer therapy, rituximab, is partially dependent on CDC for its anti-tumor activity. In preclinical studies, its antitumor activity was completely abolished in C1q-deficient mice (Di Gaetano et al., *J Immunol* 171:1581-1587, 2003). Depletion of complement also decreased its activity in a xenograft model of B cell lymphoma (Cragg and Glennie, *Blood* 103:2738-2743, 2004). It has been suggested that CDC may occur when the antibody binding site is close to the cell membrane (Pawluczkowycz et al., *J Immunol* 183:749-758, 2009). As evidence of this, ofatumumab, which binds much closer to the cell membrane than rituximab, also has much higher CDC activity (Pawluczkowycz et al., *J Immunol* 183:749-758, 2009). Almost all of the existing mesothelin mAbs and immunotoxins (including HN1 and SS1P/MORAb-009) recognize Region I, the N-terminal end of cell-surface mesothelin presumed to be located far from the cell membrane (Kaneko et al., *J Biol Chem* 284:3739-3749, 2009).

SUMMARY

Disclosed herein are mesothelin-specific, human single-domain (VH) antibodies (referred to as SD1 and SD2). The SD1 antibody binds a conformational epitope at the C-terminal end of human mesothelin and exhibits strong CDC activity, as well as ADCC, against mesothelin-expressing tumor cells. SD2 is specific for full-length human mesothelin, but does not bind a C-terminal mesothelin peptide of mesothelin.

Provided herein are monoclonal antibodies comprising one or more (such as all three) CDRs of SD1 or SD2. The antibodies provided herein include immunoglobulin molecules, such as IgG antibodies, as well as antibody fragments and single-domain (VH) antibodies. Further provided are compositions including the antibodies that bind, for example specifically bind, to mesothelin, nucleic acid molecules encoding these antibodies, expression vectors comprising the nucleic acid molecules, and isolated host cells that express the nucleic acid molecules. Also provided are immunoconjugates comprising the antibodies disclosed herein and an effector molecule, such as a toxin. Fusion proteins comprising the antibodies are also provided, such as fusion proteins comprising human Fc.

The antibodies and compositions provided herein can be used for a variety of purposes, such as for confirming the diagnosis of a cancer that expresses mesothelin, for example mesothelioma, prostate cancer, lung cancer, stomach cancer, squamous cell carcinoma, pancreatic cancer, cholangiocarcinoma, breast cancer (such as triple negative breast cancer) or ovarian cancer. Thus, provided herein is a method of confirming the diagnosis of cancer in a subject by contacting a sample from the subject diagnosed with cancer with a monoclonal antibody that binds mesothelin, and detecting binding of the antibody to the sample. An increase in binding of the antibody to the sample relative to binding of the antibody to a control sample confirms the cancer diagnosis. In some embodiments, the method further includes contacting a second antibody that specifically recognizes the mesothelin-specific antibody with the sample, and detecting binding of the second antibody.

Similarly, provided herein is a method of detecting a cancer that expresses mesothelin in a subject. The method includes contacting a sample from the subject with a monoclonal antibody described herein, and detecting binding of the antibody to the sample. An increase in binding of the antibody to the sample relative to a control sample detects cancer in the subject. In some embodiments, the methods further comprise contacting a second antibody that specifically recognizes the mesothelin-specific antibody with the sample, and detecting binding of the second antibody.

Further provided is a method of treating a subject having a mesothelin-expressing cancer, for example mesothelioma, prostate cancer, lung cancer, stomach cancer, squamous cell carcinoma, pancreatic cancer, cholangiocarcinoma breast cancer (such as triple negative breast cancer) or ovarian cancer, by selecting a subject having a cancer that expresses mesothelin and administering to the subject a therapeutically effective amount of a monoclonal antibody specific for mesothelin, or an immunoconjugate, fusion protein or composition comprising the antibody.

Also provided is a method for inhibiting tumor growth or metastasis of a mesothelin-expressing cancer in a subject by selecting a subject having a cancer that expresses mesothelin and administering to the subject a therapeutically effective amount of an antibody, immunoconjugate, fusion protein or composition disclosed herein.

The foregoing and other objects, features, and advantages of the invention will become more apparent from the following detailed description, which proceeds with reference to the accompanying figures.

BRIEF DESCRIPTION OF THE DRAWINGS

FIGS. 1A-1D: Generation of a human single-domain antibody to the C-terminal end of mesothelin. (FIG. 1A) Design of the peptide used for screening human antibodies by phage display technology. Three functional regions in membrane-bound mesothelin are proposed: Region I: 296-390; Region II: 391-486; Region III: 487-598 (of SEQ ID NO: 9). The three predicted N-linked glycans (Asn388, Asn488, and Asn515) on cell-surface mesothelin are indicated. The peptide used in the present study contains 50 residues at the C-terminal end of mesothelin (residues 539-588 of SEQ ID NO: 9). (FIG. 1B) An engineered human antibody domain (VH) phage display library was used for four rounds of phage panning on the C-terminal mesothelin peptide (residues 539-588). (FIG. 1C) Monoclonal phage ELISA experiments were performed at the end of the fourth round of panning. The SD1 phage clone (Clone 1) was selected for further analysis because it bound both full-length mesothelin and the C-terminal peptide with strong signals. (FIG. 1D) Monoclonal phage ELISA experiments were performed using two selected antibody phage clones (SD1 and SD2). The SD1 clone binds both full-length human mesothelin (MSLN) and the mesothelin peptide. The SD2 clone binds only MSLN, not the peptide.

(FIG. 2A) SDS-PAGE analysis of purified SD1-hFc (4 µg of protein per lane) under non-reducing and reducing conditions. The purity of SD1-hFc protein was greater than 95%. NR: non-reducing; R: reducing. (FIG. 2B) Immunoprecipitation of endogenous mesothelin protein in A431/H9 (forced expression of mesothelin in epidermoid carcinoma A431 cell line) (Ho et al., *Clin Cancer Res* 11:3814-3820, 2005), NCI-H226 (mesothelioma) and KMBC (cholangiocarcinoma) cell extracts. SD1 was used to immunoprecipitate endogenous mesothelin protein in the cell lysate. C: an irrelevant VH single-domain human Fc fusion; IP: immunoprecipitation; Input: western blot on whole cell lysates before immunoprecipitation.

(FIG. 3A) Direct ELISA. The SD1-hFc bound both full-length human mesothelin protein (MSLN) and peptide, but not mouse mesothelin (mMSLN) or BSA. (FIG. 3B) Competition ELISA. The mesothelin peptide, not SS1P, HN1 or an irrelevant peptide containing 50 residues, competed the binding of SD1-hFc to human mesothelin protein. (FIG. 3C) The dissociation equilibrium $K_D$ of SD1-hFc to the human mesothelin protein was 13.58 nM and (FIG. 3D) 16.08 nM for the peptide.

FIGS. 5A-5H: SD1-hFc caused CDC and ADCC against mesothelin-expressing cancer cells. (FIGS. 5A, 5B) CDC assays. A431/H9 (FIG. 5A) and NCI-H226 (FIG. 5B) cells were incubated with increasing concentrations of SD1-hFc in the presence of normal human serum (NHS, 20% vol/vol) as a source of complement. The complement protein C1q bound H9 (FIG. 5C) and NCI-H226 (FIG. 5D) cells in the presence of SD1-hFc, not HN1 or a control hFc fusion protein. (FIGS. 5E-5H) ADCC assays. Freshly isolated PBMC were incubated with target cells A431/H9 (FIG. 5E) or NCI-H226 (FIG. 5F) cells at ratio of 50:1, in the presence of SD1-hFc with increasing concentrations. Purified human NK cells were incubated with target cells A431/H9 (FIG. 5G) or NCI-H226 (FIG. 5H) at different E:T ratios with 50 µg/ml of SD1-hFc. CDC and ADCC activity were determined by LDH assay (*: $p<0.05$).

(FIG. 6A) A431/H9 cells were inoculated in the flank of nude mice to establish tumors of approximately 70 mm³ in size. From day 7, mice were treated with SD1-hFc (50 mg/kg) or PBS every other day. The down-pointing arrows indicate the day of injections. Average tumor size for each treatment group was calculated on days 7-20 (*: $p<0.05$). (FIG. 6B) A431/H9 cells were incubated with 100 µg/mL of SD1-hFc in the presence of normal mouse serum (30% vol/vol) as a source of mouse complement. CDC activity was measured by LDH assay (*: $p<0.05$). (FIG. 6C) A431/H9 cells were incubated with 100 µg/mL of SD1-hFc in the presence of purified mouse NK cells as a source of mouse effector cells. Mouse ADCC activity was measured by LDH assay (*: $p<0.05$). (FIG. 6D) The purity of mouse NK cells.

(FIG. 7A) SDS-PAGE analysis of purified SD1-PE38 (4 µg of protein per lane) under non-reducing condition. The purity of SD1-PE38 was greater than 95%. IT: immunotoxin. (FIG. 7B) WST-8 assays on A431/H9, A431, NCI-H226, and KMBC cells treated with the SD1-PE38 immunotoxin.

SEQUENCE LISTING

Figure 1C:
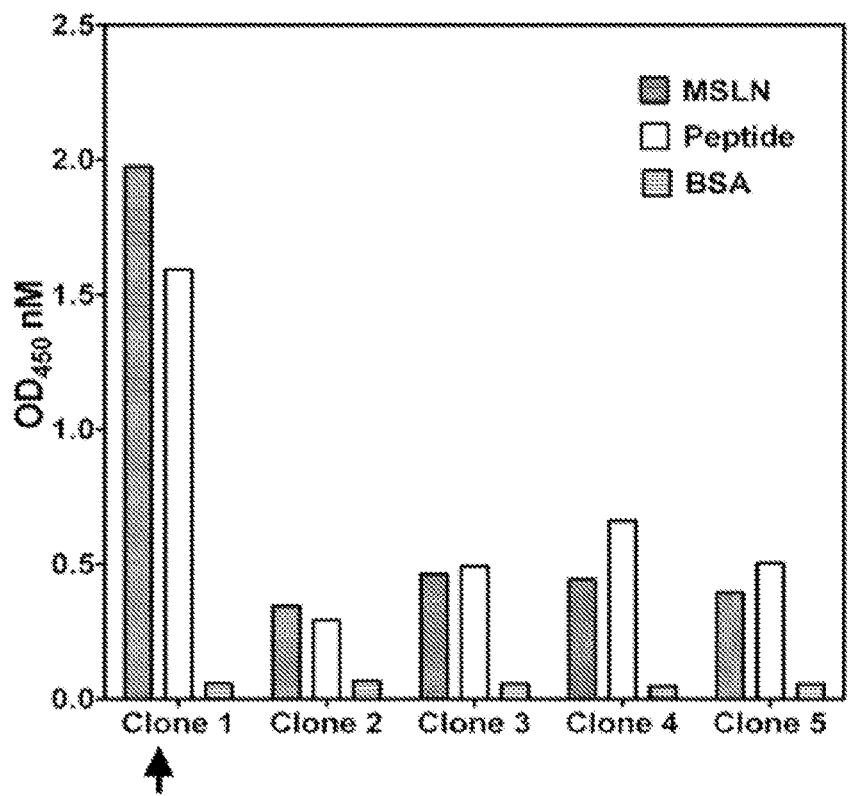

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Feb. 26, 2015, 26.7 KB, which is incorporated by reference herein. In the accompanying sequence listing:

SEQ ID NO: 1 is the nucleotide sequence of the SD1 single-domain antibody.

SEQ ID NO: 2 is the amino acid sequence of the SD1 single-domain antibody.

SEQ ID NO: 3 is the amino acid sequence of *Pseudomonas* exotoxin (PE).

SEQ ID NO: 4 is the amino acid sequence of PE38.

SEQ ID NO: 5 is the amino acid sequence of PE-LR.

SEQ ID NO: 6 is the amino acid sequence of PE-LR/6X.

SEQ ID NO: 7 is the amino acid sequence of PE with reduced immunogenicity.

SEQ ID NO: 8 is the amino acid sequence of PE-LR/8M.

SEQ ID NO: 9 is the amino acid sequence of human mesothelin.

SEQ ID NOs: 10-13 are primer sequences.

SEQ ID NO: 14 is the nucleotide sequence of the SD2 single-domain antibody.

SEQ ID NO: 15 is the amino acid sequence of the SD2 single-domain antibody.

DETAILED DESCRIPTION

I. Abbreviations

ADCC antibody-dependent cell-mediated cytotoxicity
CAR chimeric antigen receptor
CDC complement-dependent cytotoxicity
cDNA complementary DNA
CDR complementarity determining region
CTL cytotoxic T lymphocyte
ELISA enzyme-linked immunosorbent assay
EM effector molecule
FACS fluorescence activated cell sorting
GPI glycosylphosphatidylinositol
hFc human Fc
HRP horseradish peroxidase
Ig immunoglobulin
i.v. intravenous
$K_D$ dissociation constant
LDH lactate dehydrogenase
mAb monoclonal antibody
MAC membrane attack complex
mMSLN murine mesothelin
MSLN mesothelin
NHS normal human serum
PBMC peripheral blood mononuclear cells
PCR polymerase chain reaction
PE *Pseudomonas* exotoxin
PE phycoerythrin
pfu plaque forming units
RIPA radioimmunoprecipitation assay
VH variable heavy
VL variable light II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Antibody: A polypeptide ligand comprising at least a light chain or heavy chain immunoglobulin variable region which recognizes and binds (such as specifically recognizes and specifically binds) an epitope of an antigen, such as mesothelin, or a fragment thereof. Immunoglobulin molecules are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as single-domain antibodies (e.g. VH domain antibodies), Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term "antibody" also includes genetically engineered forms such as chimeric antibodies (for example, humanized murine antibodies) and heteroconjugate antibodies (such as bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined according to Kabat et al. (see, Kabat et al., *Sequences of Proteins of Immunological Interest*, U.S. Department of Health and Human Services, 1991) and the ImMunoGeneTics database (IMGT) (see, Lefranc, *Nucleic Acids Res* 29:207-9, 2001). The IMGT and Kabat databases are available online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are often identified by the chain in which the particular CDR is located. Thus, a $V_H$ CDR3 (or H-CDR3) is located in the variable domain of the heavy chain of the antibody in which it is found, whereas a $V_L$ CDR1 (or L-CDR1) is the CDR1 from the variable domain of the light chain of the antibody in which it is found. An antibody that binds mesothelin, for example, will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and/or heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" contains structural elements from two or more different antibody molecules, often from different animal species. For example, a chimeric antibody can have framework residues from one species, such as human, and CDRs (which generally confer antigen binding) from another species, such as a murine antibody that specifically binds mesothelin.

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. A "humanized" immunoglobulin is an immunoglobulin including a human framework region and one or more CDRs from a non-human (for example a mouse, rabbit, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

Binding affinity: Affinity of an antibody for an antigen. In one embodiment, affinity is calculated by a modification of the Scatchard method described by Frankel et al. (*Mol. Immunol.*, 16:101-106, 1979). In another embodiment, binding affinity is measured by an antigen/antibody dissociation rate. In another embodiment, a high binding affinity is measured by a competition radioimmunoassay. In another embodiment, binding affinity is measured by ELISA. An antibody that "specifically binds" an antigen (such as mesothelin) is an antibody that binds the antigen with high affinity and does not significantly bind other unrelated antigens.

Breast cancer: A type of cancer that forms in tissues of the breast, usually the ducts (tubes that carry milk to the nipple) and lobules (glands that make milk). Triple negative breast cancer refers to a type of breast cancer in which the cancer cells do not express estrogen receptors, progesterone receptors or significant levels of HER2/neu protein. Triple negative breast cancer is also called ER-negative PR-negative HER2/neu-negative breast cancer.

Chemotherapeutic agent: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating mesothelioma or another tumor, such as stomach cancer, squamous cell carcinomas, prostate cancer, pancreatic cancer, lung cancer, cholangiocarcinoma breast cancer (such as triple negative breast cancer) or ovarian cancer. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., ©2000 Churchill Livingstone, Inc; Baltzer, L., Berkery, R. (eds.): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody (or immunoconjugate) that binds mesothelin used in combination with a radioactive or chemical compound.

Cholangiocarcinoma: A type of cancer that develops in cells that line the bile ducts in the liver.

Conservative variant: "Conservative" amino acid substitutions are those substitutions that do not substantially affect or decrease the affinity of a protein, such as an antibody to mesothelin. For example, a monoclonal antibody that specifically binds mesothelin can include at most about 1, at most about 2, at most about 5, at most about 10, or at most about 15 conservative substitutions and specifically bind a mesothelin polypeptide. The term "conservative variant" also includes the use of a substituted amino acid in place of an unsubstituted parent amino acid, provided that antibody specifically binds mesothelin. Non-conservative substitutions are those that reduce an activity or binding to mesothelin.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Complementarity determining region (CDR): Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively.

Contacting: Placement in direct physical association; includes both in solid and liquid form.

Cytotoxicity: The toxicity of a molecule, such as an immunotoxin, to the cells intended to be targeted, as opposed to the cells of the rest of an organism. In one embodiment, in contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Degenerate variant: In the context of the present disclosure, a "degenerate variant" refers to a polynucleotide encoding a mesothelin polypeptide or an antibody that binds mesothelin that includes a sequence that is degenerate as a result of the genetic code. There are 20 natural amino acids, most of which are specified by more than one codon. Therefore, all degenerate nucleotide sequences are included as long as the amino acid sequence of the mesothelin polypeptide or antibody that binds mesothelin encoded by the nucleotide sequence is unchanged.

Diagnostic: Identifying the presence or nature of a pathologic condition, such as, but not limited to, cancer. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as cancer or metastasis.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms.

Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-mesothelin antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art (see, for example, U.S. Pat. No. 4,957,735; and Connor et al., *Pharm Ther* 28:341-365, 1985). Diagnostic agents or moieties include radioisotopes and other detectable labels. Detectable labels useful for such purposes are also well known in the art, and include radioactive isotopes such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$, fluorophores, chemiluminescent agents, and enzymes.

Epitope: An antigenic determinant. These are particular chemical groups or peptide sequences on a molecule that are antigenic, i.e. that elicit a specific immune response. An antibody specifically binds a particular antigenic epitope on a polypeptide, such as mesothelin.

Framework region: Amino acid sequences interposed between CDRs. Framework regions include variable light and variable heavy framework regions. The framework regions serve to hold the CDRs in an appropriate orientation for antigen binding.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Hybridoma: A hybrid cell for the production of monoclonal antibodies. A hybridoma is produced by fusion of an antibody-producing cell (such as a B cell obtained from an immunized animal, for example a mouse, rat or rabbit) and a myeloma cell.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a $CD4^+$ response or a $CD8^+$ response. In another embodiment, the response is a B cell response, and results in the production of specific antibodies.

Immunoconjugate: A covalent linkage of an effector molecule to an antibody or functional fragment thereof. The effector molecule can be a detectable label or an immunotoxin. Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody. A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody is joined to an effector molecule. In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand or an antibody, conjugated (coupled) to an effector molecule.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Lung cancer: Cancer that forms in tissues of the lung, usually in the cells lining air passages. The two main types are small cell lung cancer and non-small cell lung cancer (NSCLC). These types are diagnosed based on how the cells look under a microscope.

Mammal: This term includes both human and non-human mammals. Similarly, the term "subject" includes both human and veterinary subjects.

Mesothelin: A 40 kDa cell-surface glycosylphosphatidylinositol (GPI)-linked glycoprotein. The human mesothelin protein is synthesized as a 70 kD precursor which is then proteolytically processed. The 30 kD amino terminus of mesothelin is secreted and is referred to as megakaryocyte potentiating factor (Yamaguchi et al., *J. Biol. Chem.* 269:805 808, 1994). The 40 kD carboxyl terminus remains bound to the membrane as mature mesothelin (Chang et al., *Natl. Acad. Sci. USA* 93:136 140, 1996). Exemplary nucleic acid and amino acid sequences of mesothelin are as described in PCT Publication No. WO 97/25,068; U.S. Pat. No. 6,083,502; Chang and Pastan, *Int. J. Cancer* 57:90, 1994; Chang and Pastan, *Proc. Natl. Acad. Sci USA* 93:136, 1996; Brinkmann et al., *Int. J. Cancer* 71:638, 1997; and Chowdhury et al., *Mol. Immunol.* 34:9, 1997. The amino acid sequence of human mesothelin is set forth herein as SEQ ID NO: 9. Mesothelin also refers to mesothelin proteins or polypeptides which remain intracellular as well as secreted and/or isolated extracellular mesothelin protein.

Mesothelioma: A type of neoplasm derived from the lining cells of the pleura and peritoneum which grows as a thick sheet covering the viscera, and is composed of spindle cells or fibrous tissue which may enclose gland-like spaces lined by cuboidal cells. Mesotheliomas often originate in the tissue lining the lung, heart or abdomen. In some cases, mesotheliomas are caused by exposure to asbestos.

MORAb-009: A chimeric (mouse/human) monoclonal IgG/κ with high affinity and specificity for mesothelin. The VH and VL regions of mouse anti-mesothelin scFv were obtained by panning a phage display library made from splenic mRNA of a mouse immunized with mesothelin cDNA on mesothelin-positive cells. The VH and VL regions were grafted in frame with human IgG1 and kappa constant regions (Hassan and Ho, *Eur J Cancer* 44(1):46-53, 2008).

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, cholangiocarcinoma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma.

In several examples, the cancer is mesothelioma, stomach cancer, squamous cell carcinomas, prostate cancer, pancreatic cancer, lung cancer, cholangiocarcinoma, breast cancer or ovarian cancer.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Ovarian cancer: Cancer that forms in tissues of the ovary (one of a pair of female reproductive glands in which the ova, or eggs, are formed). Most ovarian cancers are either ovarian epithelial carcinomas (cancer that begins in the cells on the surface of the ovary) or malignant germ cell tumors (cancer that begins in egg cells).

Pancreatic cancer: A disease in which malignant (cancer) cells are found in the tissues of the pancreas. Also called exocrine cancer.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the antibodies disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Prostate cancer: Cancer that forms in tissues of the prostate (a gland in the male reproductive system found below the bladder and in front of the rectum). Prostate cancer usually occurs in older men.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Recombinant toxins: Chimeric proteins in which a cell targeting moiety is fused to a toxin (Pastan et al., *Science*, 254:1173-1177, 1991). If the cell targeting moiety is the Fv portion of an antibody, the molecule is termed a recombinant immunotoxin (Chaudhary et al., *Nature*, 339:394-397, 1989). The toxin moiety is genetically altered so that it cannot bind to the toxin receptor present on most normal cells. Recombinant immunotoxins selectively kill cells which are recognized by the antigen binding domain. These recombinant toxins and immunotoxins can be used to treat cancer, for example, a cancer in which mesothelin is expressed.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material. In one example, a sample includes a tumor biopsy, such as a tumor biopsy.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, Gene 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds mesothelin or a fragment thereof are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Squamous cell carcinoma: A malignant neoplasm derived from stratified squamous epithelium, but which may also occur in sites such as bronchial mucosa where glandular or columnar epithelium is normally present. Squamous cell carcinoma is the most common type of skin cancer.

SS1P: A recombinant immunotoxin consisting of an anti-mesothelin Fv (the same Fv as MORAb-009) linked to a truncated *Pseudomonas* exotoxin that mediates cell killing (Chowdhury and Pastan, *Nat Biotechnol* 17:568-572, 1999; Pastan et al., *Nat Rev Cancer* 6:559-565, 2006). SS1P, also known as CAT-5001, is cytotoxic to cell lines expressing mesothelin, causes complete regression of mesothelin expressing tumor xenografts in nude mice, and is cytotoxic to cells obtained from human cancer patients (Hassan et al., *Clin Cancer Res* 10:3937-3942, 2001; Hassan et al., *Clin Cancer Res* 8:3520-3526, 2002).

Stomach cancer: Cancer that forms in tissues lining the stomach. Also called gastric cancer.

Subject: Living multi-cellular vertebrate organisms, a category that includes both human and veterinary subjects, including human and non-human mammals.

Synthetic: Produced by artificial means in a laboratory, for example a monoclonal antibody produced by hybridoma technology or expressed from a cDNA construct.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate, reduce the size, or prevent metastasis of a tumor. When administered to a subject, a dosage will generally be used that will achieve target tissue concentrations (for example, in tumors) that has been shown to achieve a desired in vitro effect.

Toxin: A molecule that is cytotoxic for a cell. Toxins include abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Monoclonal antibodies against mesothelin are currently being evaluated for the treatment of mesothelioma and multiple other forms of cancer, and show great promise for clinical development for solid cancers. Antibodies against mesothelin have been shown to act via immunotoxin-based inhibition of tumor growth and induction of antibody-dependent cellular cytotoxicity (ADCC). However, complement-dependent cytotoxicity (CDC), which is considered one of the most important cell killing mechanisms of therapeutic antibodies against tumors, is inactive for such antibodies. Disclosed herein is the use of phage display antibody engineering technology and synthetic peptide screening to identify SD1, a human single-domain antibody to mesothelin. SD1 recognizes a conformational epitope at the C-terminal end (residues 539-588 of SEQ ID NO: 9) of mesothelin close to the cell surface. Also identified was SD2, a single-domain antibody that recognizes full-length mesothelin. To investigate SD1 as a potential therapeutic agent, a recombinant human Fc (SD1-hFc) fusion protein was generated. The SD1-hFc protein exhibits strong CDC activity, in addition to ADCC, against mesothelin-expressing tumor cells. Furthermore, the SD1-hFc protein causes significant tumor growth inhibition of tumor xenografts in nude mice. SD1 is the first human single-domain antibody targeting mesothelin-expressing tumors. The results disclosed herein demonstrate that SD1 can be used as a therapeutic agent for cancer and exhibits significant advantages over current antibody therapy targeting mesothelin-expressing tumors.

IV. Mesothelin-Specific Monoclonal Antibodies

Disclosed herein are SD1 and SD2, human single-domain antibodies specific for mesothelin. In contrast to previously described mesothelin-specific therapeutic antibodies, SD1 recognizes a conformational epitope at the C-terminal end of mesothelin. When fused to human Fc, SD1 elicits strong CDC and ADCC against mesothelin-expressing tumor cells. It is also demonstrated herein that SD1-hFc significantly inhibits tumor growth in vivo in a mouse xenograft model of mesothelin-expressing cancer. SD2 recognizes full-length mesothelin, but does not bind a C-terminal fragment of mesothelin. The nucleotide and amino acid sequences of SD1 and SD2 are shown below.

SD1 nucleotide sequence (SEQ ID NO: 1):
CAGGTGCAGCTGGTGCAGTCTGGGGGAGGCTTGGTACAG

CCTGGAGGGTCCCTGAGACTCTCCTGTGCAGCCTCTGAT

TTCGATTTCGCTGCTTATGAAATGAGCTGGGTCCGCCAG

GCTCCAGGACAAGGCCTTGAGTGGGTGGCAATTATATCA

CATGATGGAATCGATAAATACTACACAGACTCCGTGAAG

GGCCGATTCACCATCTCCAGAGACAATTCCAAGAACACG

CTGTATCTGCAAATGAACACCCTGAGAGCCGAGGACACA

GCCACGTATTACTGTTTAAGGCTTGGTGCTGTAGGCCAG

GGAACCCTGGTCACCGTCTCCTCAAGT

SD1 amino acid sequence (SEQ ID NO: 2):
QVQLVQSGGGLVQPGGSLRLSCAASDFDFAAYEMSWVRQ

APGQGLEWVAIISHDGIDKYYTDSVKGRFTISRDNSKNT

LYLQMNTLRAEDTATYYCLRLGAVGQGTLVTVSSS

TABLE 1

CDR positions of SD1 (SEQ ID NO: 2)

| System | CDR1 | CDR2 | CDR3 |
|---|---|---|---|
| Kabat | 31-35 | 51-66 | 99-102 |
| IMGT | 26-35 | 51-58 | 97-103 |

SD2 nucleotide sequence (SEQ ID NO: 14):
CAGGTGCAGCTGGTGCAGTCTGGGGGAGGCTTGGTACAGC

CTGGAGGGTCCCTGAGACTCTCCTGTGCAGCCTCTGATTT

CGCTTTCGATGATTATGAAATGAGCTGGGTCCGCCAGGCT

CCAGGAAAGGCCCTTGAGTGGATTGGGGACATCAATCATA

GTGGAACCACCATCTACAACCCGTCCCTCAAGAGTCGAGT

CACCATCTCCAGAGACAATTCCAAGAACACGCTGTATCTG

CAAATGAACACCCTGAGAGCCGAGGACACAGCCATATATT

ACTGTGCGAGACCTCACTACGGTGACTACTCTGATGCTTT

TGATATCTGGGGCCAAGGGACAATGGTCACCGTCTCCTCA

AGT

SD2 amino acid sequence (SEQ ID NO: 15):
QVQLVQSGGGLVQPGGSLRLSCAASDFAFDDYEMSWVRQA

PGKALEWIGDINHSGTTIYNPSLKSRVTISRDNSKNTLYL

QMNTLRAEDTAIYYCARPHYGDYSDAFDIWGQGTMVTVSS

S

TABLE 2

CDR positions of SD2 (SEQ ID NO: 15)

| System | CDR1 | CDR2 | CDR3 |
|---|---|---|---|
| Kabat | 31-35 | 50-65 | 99-106 |
| IMGT | 26-33 | 51-57 | 96-111 |

Provided herein are isolated monoclonal antibodies that bind (for example, specifically bind) mesothelin, such as cell-surface or soluble mesothelin. In some embodiments, the VH domain of the antibody comprises at least a portion of the amino acid sequence set forth herein as SEQ ID NO: 2 or SEQ ID NO: 15, such as one or more (such as all three) CDR sequences from SEQ ID NO: 2 or SEQ ID NO: 15 as determined by IMGT. In other embodiments, the antibodies comprise one or more (such as all three) CDR sequences from SEQ ID NO: 2 or SEQ ID NO: 15, as determined using the Kabat method.

In some embodiments, the VH domain of the antibody comprises amino acid residues 26-35, 51-58 and 97-103 of SEQ ID NO: 2. In other embodiments, the VH domain of the antibody comprises amino acid residues 31-35, 51-66 and 99-102 of SEQ ID NO: 2. In some examples, the VH domain of the antibody is at least 90%, at least 95%, at least 96%, at least 97%, at least 98% or at least 99% identical to SEQ ID NO: 2. In particular examples, the amino acid sequence of the VH domain of the antibody comprises or consists of SEQ ID NO: 2.

In other embodiments, the VH domain of the antibody comprises amino acid residues 26-33, 51-57 and 96-111 of SEQ ID NO: 15. In other embodiments, the VH domain of the antibody comprises amino acid residues 31-35, 50-65 and 99-106 of SEQ ID NO: 15. In some examples, the VH domain of the antibody is at least 90%, at least 95%, at least 96%, at least 97%, at least 98% or at least 99% identical to SEQ ID NO: 15. In particular examples, the amino acid sequence of the VH domain of the antibody comprises or consists of SEQ ID NO: 15.

In some embodiments, the monoclonal antibody that binds, such as specifically binds, mesothelin is a single domain antibody.

In some embodiments, the monoclonal antibody that binds, such as specifically binds, mesothelin is a Fab fragment, a Fab' fragment, a F(ab)'$_2$ fragment, a single chain variable fragment (scFv), or a disulfide stabilized variable fragment (dsFv). In other embodiments, the antibody is an immunoglobulin molecule. In particular examples, the antibody is an IgG.

In some embodiments, the monoclonal antibody is chimeric or synthetic.

In some embodiments, the disclosed antibodies bind mesothelin (soluble or cell-surface mesothelin) with a dissociation constant ($K_d$) of about 20 nM or less, such as about 18 nM or less, 16 nM or less, 14 nM or less, 12 nM or less or 10 nM or less. In several embodiments, the monoclonal antibodies bind mesothelin with a binding affinity of about 20 nM, about 19 nM, about 17 nM, about 16 nM, about 15 nM, about 14 nM, about 13 nM, about 12 nM, about 11 nM, or about 10 nM.

The monoclonal antibodies disclosed herein can be labeled, such as with a fluorescent, enzymatic, or radioactive label.

Immunoconjugates comprising the monoclonal antibodies disclosed herein and an effector molecule are also provided. The effector molecule can be, for example, a toxin or a detectable label. In some embodiments, the immunoconjugate comprises a VH domain disclosed herein (such as a VH domain comprising the CDR sequences of SD1 or SD2, or comprising the amino acid sequence of SEQ ID NO: 2 or SEQ ID NO: 15), and a toxin, such as PE or a variant therefore, such as PE38. In particular examples, the immunoconjugate comprises the SD1 or SD2 VH fused to PE38. In some examples, the toxin is PE38 comprising the amino acid sequence of SEQ ID NO: 4. Examples of immunoconjugates are discussed in greater detail in section VI below.

Also provided are fusion proteins comprising an antibody disclosed herein and a heterologous protein. In some examples, the heterologous protein is an Fc protein. In one non-limiting example, the Fc protein is a human Fc protein, such as human IgGγ1 Fc.

Further provided herein are compositions comprising a therapeutically effective amount of a disclosed antibody, immunoconjugate or fusion protein and a pharmaceutically acceptable carrier.

Also provided herein are isolated nucleic acid molecules encoding the disclosed monoclonal antibodies, immunoconjugates and fusion proteins. In some embodiments, the nucleotide sequence encoding the VH domain of the monoclonal antibody comprises at least a portion of SEQ ID NO: 1, such as the portion encoding one or more CDRs of the antibody. In some examples, the VH domain of the monoclonal antibody is encoded by a sequence comprising SEQ ID NO: 1. In other embodiments, the nucleotide sequence encoding the VH domain of the monoclonal antibody comprises at least a portion of SEQ ID NO: 14, such as the portion encoding one or more CDRs of the antibody. In some examples, the VH domain of the monoclonal antibody is encoded by a sequence comprising SEQ ID NO: 14.

In some examples, the isolated nucleic acid molecule is operably linked to a promoter.

Also provided are expression vectors comprising the isolated nucleic acid molecules disclosed herein. Isolated host cells comprising the nucleic acid molecules or vectors are also provided herein. In some examples, the host cell is a T cell, such as a cytotoxic T lymphocyte (CTL).

V. Antibodies and Antibody Fragments

The monoclonal antibodies disclosed herein can be of any isotype. The monoclonal antibody can be, for example, an IgM or an IgG antibody, such as IgG$_1$ or an IgG$_2$. The class of an antibody that specifically binds mesothelin can be switched with another (for example, IgG can be switched to IgM), according to well-known procedures. Class switching can also be used to convert one IgG subclass to another, such as from IgG$_1$ to IgG$_2$.

Antibody fragments are also encompassed by the present disclosure, such as single-domain antibodies (e.g., VH domain antibodies), Fab, F(ab')$_2$, and Fv. These antibody fragments retain the ability to selectively bind with the antigen. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains;

(5) Single chain antibody (such as scFv), a genetically engineered molecule containing the variable region of the light chain, the variable region of the heavy chain, linked by a suitable polypeptide linker as a genetically fused single chain molecule;

(6) A dimer of a single chain antibody (scFV$_2$), defined as a dimer of a scFV (also known as a "miniantibody"); and (7) VH single-domain antibody, an antibody fragment consisting of a heavy chain variable domain.

Methods of making these fragments are known in the art (see for example, Harlow and Lane, *Antibodies: A Laboratory Manual*, Cold Spring Harbor Laboratory, New York, 1988).

In some cases, antibody fragments can be prepared by proteolytic hydrolysis of the antibody or by expression in a host cell (such as *E. coli*) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the V$_H$ and the V$_L$ regions, and will retain the charge characteristics of the residues in order to preserve the low pI and low toxicity of the molecules Amino acid substitutions (such as at most one, at most two, at most three, at most four, or at most five amino acid substitutions) can be made in the V$_H$ and/or the V$_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

VI. Immunoconjugates and Fusion Proteins

The disclosed monoclonal antibodies specific for mesothelin can be conjugated to a therapeutic agent or effector molecule Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents can include various drugs such as vinblastine, daunomycin and the like, cytotoxins such as native or modified *Pseudomonas* exotoxin or Diphtheria toxin, encapsulating agents (such as liposomes) which themselves contain pharmacological compositions, radioactive agents such as $^{125}$I, $^{32}$P, $^{14}$C, $^{3}$H and $^{35}$S and other labels, target moieties and ligands.

The choice of a particular therapeutic agent depends on the particular target molecule or cell, and the desired biological effect. Thus, for example, the therapeutic agent can be a cytotoxin that is used to bring about the death of a particular target cell (such as a tumor cell). Conversely, where it is desired to invoke a non-lethal biological response, the therapeutic agent can be conjugated to a non-lethal pharmacological agent or a liposome containing a non-lethal pharmacological agent.

With the therapeutic agents and antibodies described herein, one of skill can readily construct a variety of clones containing functionally equivalent nucleic acids, such as nucleic acids which differ in sequence but which encode the same effector moiety or antibody sequence. Thus, the present disclosure provides nucleic acids encoding antibodies and conjugates and fusion proteins thereof.

Effector molecules can be linked to an antibody of interest using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine ($-NH_2$) or sulfhydryl ($-SH$) groups, which are available for reaction with a suitable functional group on an antibody to result in the binding of the effector molecule. Alternatively, the antibody is derivatized to expose or attach additional reactive functional groups. The derivatization may involve attachment of any of a number of known linker molecules. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, label (such as enzymes or fluorescent molecules) drugs, toxins, and other agents to antibodies one skilled in the art will be able to determine a suitable method for attaching a given agent to an antibody or other polypeptide.

The antibodies or antibody fragments disclosed herein can be derivatized or linked to another molecule (such as another peptide or protein). In some cases, the antibody or antibody fragment (such as a VH domain) is fused to a heterologous protein, for example an Fc protein.

In general, the antibodies or portion thereof is derivatized such that the binding to the target antigen is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available.

An antibody that binds (for example specifically binds) mesothelin or a fragment thereof can be labeled with a detectable moiety. Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody may also be labeled with biotin, and detected through indirect measurement of avidin or streptavidin binding. It should be noted that the avidin itself can be labeled with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect mesothelin by x-ray, emission spectra, or other diagnostic techniques. Examples of labels for polypeptides include, but are not limited to, the following radioisotopes or radionucleotides: $^{3}$H, $^{14}$C, $^{15}$N, $^{35}$S, $^{90}$Y, $^{99}$Tc, $^{111}$In, $^{125}$I, $^{131}$I.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Toxins can be employed with the monoclonal antibodies described herein to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, Mo.). Contemplated toxins also include variants of the toxins described herein (see, for example, see, U.S. Pat. Nos. 5,079,163 and 4,689,401). In one embodiment, the toxin is *Pseudomonas* exotoxin (PE) (U.S. Pat. No. 5,602,095). As used herein "*Pseudomonas* exotoxin" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., *J. Biol. Chem.* 264:14256-14261, 1989).

PE employed with the monoclonal antibodies described herein can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; PCT Publication No. WO 99/51643; Pai et al., *Proc. Natl. Acad. Sci. USA* 88:3358-3362, 1991; Kondo et al., *J. Biol. Chem.* 263:9470-9475, 1988; Pastan et al., *Biochim. Biophys. Acta* 1333:C1-C6, 1997.

The full-length PE sequence is set forth herein as SEQ ID NO: 3:

AEEAFDLWNECAKACVLDLKDGVRSSRMSVDPAIADTNGQGVLHYSM

VLEGGNDALKLAIDNALSITSDGLTIRLEGGVEPNKPVRYSYTRQAR

GSWSLNWLVPIGHEKPSNIKVFIHELNAGNQLSHMSPIYTIEMGDEL

LAKLARDATFFVRAHESNEMQPTLAISHAGVSVVMAQTQPRREKRWS

EWASGKVLCLLDPLDGVYNYLAQQRCNLDDTWEGKIYRVLAGNPAKH

DLDIKPTVISHRLHFPEGGSLAALTAHQACHLPLETFTRHRQPRGWE

QLEQCGYPVQRLVALYLAARLSWNQVDQVIRNALASPGSGGDLGEAI

REQPEQARLALTLAAAESERFVRQGTGNDEAGAANADVVSLTCPVAA

GECAGPADSGDALLERNYPTGAEFLGDGGDVSFSTRGTQNWTVERLL

QAHRQLEERGYVFVGYHGTFLEAAQSIVFGGVRARSQDLDAIWRGFY

IAGDPALAYGYAQDQEPDARGRIRNGALLRVYVPRSSLPGFYRTSLT

LAAPEAAGEVERLIGHPLPLRLDAITGPEEEGGRLETILGWPLAERT

VVIPSAIPTDPRNVGGDLDPSSIPDKEQAISALPDYASQPGKPPRED

LK

In some examples, the PE is PE38, comprising the following amino acid sequence:

(SEQ ID NO: 4)
GGSLAALTAHQACHLPLETFTRHRQPRGWEQLEQCGYPVQRLVALYL

AARLSWNQVDQVIRNALASPGSGGDLGEAIREQPEQARLALTLAAAE

SERFVRQGTGNDEAGAANGPADSGDALLERNYPTGAEFLGDGGDVSF

STRGTQNWTVERLLQAHRQLEERGYVFVGYHGTFLEAAQSIVFGGVR

ARSQDLDAIWRGFYIAGDPALAYGYAQDQEPDARGRIRNGALLRVYV

PRSSLPGFYRTSLTLAAPEAAGEVERLIGHPLPLRLDAITGPEEEGG

RLETILGWPLAERTVVIPSAIPTDPRNVGGDLDPSSIPDKEQAISAL

PDYASQPGKPPREDLK

Also contemplated herein are protease-resistant PE variants and PE variants with reduced immunogenicity, such as, but not limited to PE-LR, PE-6X, PE-8X, PE-LR/6X and PE-LR/8X (see, for example, Weldon et al., *Blood* 113(16): 3792-3800, 2009; Onda et al., *Proc Natl Acad Sci USA* 105 (32):11311-11316, 2008; and PCT Publication Nos. WO 2007/016150, WO 2009/032954 and WO 2011/032022).

In some examples, the PE is a variant that is resistant to lysosomal degradation, such as PE-LR (Weldon et al., *Blood* 113(16):3792-3800, 2009; PCT Publication No. WO 2009/032954) having the following amino acid sequence:

(SEQ ID NO: 5)
RHRQPRGWEQLPTGAEFLGDGGDVSFSTRGTQNWTVERLLQAHRQLE

ERGYVFVGYHGTFLEAAQSIVFGGVRARSQDLDAIWRGFYIAGDPAL

AYGYAQDQEPDARGRIRNGALLRVYVPRSSLPGFYRTSLTLAAPEAA

GEVERLIGHPLPLRLDAITGPEEEGGRLETILGWPLAERTVVIPSAI

PTDPRNVGGDLDPSSIPDKEQAISALPDYASQPGKPPREDLK

In other examples, the PE is a variant designated PE-LR/6X (PCT Publication No. WO 2011/032022) having the following amino acid sequence:

(SEQ ID NO: 6)
RHRQPRGWEQLPTGAEFLGDGGDVSFSTRGTQNWTVERLLQAHRQLE

EGGYVFVGYHGTFLEAAQSIVFGGVRARSQDLDAIWAGFYIAGDPAL

AYGYAQDQEPDAAGRIRNGALLRVYVPRSSLPGFYATSLTLAAPEAA

GEVERLIGHPLPLRLDAITGPEESGGRLETILGWPLAERTVVIPSAI

PTDPRNVGGDLDPSSIPDSEQAISALPDYASQPGKPPREDLK

In other examples, the PE variant is PE with reducing immunogenicity, such as a PE with the following sequence:

(X = G, A or S; SEQ ID NO: 7)
RHRQPRGWEQLPTGAEFLGDGGXVSFSTRGTQNWTVERLLQAHRQLE

EXGYVFVGYHGTFLEAAQSIVFGGVRARSQDLDAIWXGFYIAGDPAL

AYGYAQDQEPDAXGRIRNGALLRVYVPRSSLPGFYXTSLTLAAPEAA

GEVERLIGHPLPLRLDAITGPEEXGGRLETILGWPLAERTVVIPSAI

PTDPRNVGGDLDPSSIPDXEXAISALPDYASQPGKPPREDLK

In other examples, the PE is a variant designated PE-LR/8M (PCT Publication No. WO 2011/032022) having the following amino acid sequence:

(SEQ ID NO: 8)
RHRQPRGWEQLPTGAEFLGDGGAVSFSTRGTQNWTVERLLQAHRQLE

EGGYVFVGYHGTFLEAAQSIVFGGVRARSQDLDAIWAGFYIAGDPAL

AYGYAQDQEPDAAGRIRNGALLRVYVPRSSLPGFYATSLTLAAPEAA

GEVERLIGHPLPLRLDAITGPEESGGRLETILGWPLAERTVVIPSAI

PTDPRNVGGDLDPSSIPDSEAAISALPDYASQPGKPPREDLK

Substitutions of PE are defined herein by reference to the amino acid sequence of full-length PE set forth herein as SEQ ID NO: 3. Substitutions of PE are described herein by reference to the amino acid residue present at a particular position, followed by the amino acid with which that residue has been replaced in the particular substitution. In this regard, the positions of the amino acid sequence of a particular embodiment of a PE are referred to herein as the positions of the amino acid sequence of the particular embodiment, or as the positions as defined by SEQ ID NO: 3. Thus, substitutions refer to a replacement of an amino acid residue in the amino acid sequence of a particular embodiment of a PE corresponding to the indicated position of the 613-amino acid sequence of SEQ ID NO: 3 with the understanding that the actual positions in the respective amino acid sequence may be different. In the event of multiple substitutions at two or more positions, the two or more substitutions may be the same or different—each amino acid residue of the two or more amino acid residues being substituted can be substituted with the same or different amino acid residue unless explicitly indicated otherwise.

Modification of PE may occur in any previously described variant, including cytotoxic fragments of PE (for example, PE38, PE-LR and PE-LR/8M). Modified PEs may include any substitution(s), as described above, for one or more amino acid residues within one or more T-cell epitopes and/or B cell epitopes of PE.

The antibodies described herein can also be used to target any number of different diagnostic or therapeutic compounds to cells expressing mesothelin on their surface. Thus, an antibody of the present disclosure can be attached directly or via a linker to a drug that is to be delivered directly to cells expressing cell-surface mesothelin. This can be done for therapeutic, diagnostic or research purposes. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-mesothelin antibody can be an encapsulation system, such as a liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are well known to those of skill in the art (see, for example, U.S. Pat. No. 4,957,735; Connor et al., *Pharm. Ther.* 28:341-365, 1985).

Antibodies described herein can also be covalently or non-covalently linked to a detectable label. Detectable labels suitable for such use include any composition detectable by spectroscopic, photochemical, biochemical, immunochemical, electrical, optical or chemical means. Useful labels include magnetic beads, fluorescent dyes (for example, fluorescein isothiocyanate, Texas red, rhodamine, green fluorescent protein, and the like), radiolabels (for example, $^3$H, $^{125}$I, $^{35}$S, $^{14}$C, or $^{32}$P), enzymes (such as horseradish peroxidase, alkaline phosphatase and others commonly used in an ELISA), and colorimetric labels such as colloidal gold or colored glass or plastic (such as polystyrene, polypropylene, latex, and the like) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

VII. Compositions and Methods of Use

Compositions are provided that include one or more of the disclosed antibodies that bind (for example specifically bind) mesothelin in a carrier. Compositions comprising fusion proteins, immunoconjugates or immunotoxins are also provided. The compositions can be prepared in unit dosage forms for administration to a subject. The amount and timing of administration are at the discretion of the treating clinician to achieve the desired outcome. The antibody can be formulated for systemic or local (such as intra-tumor) administration. In one example, the antibody is formulated for parenteral administration, such as intravenous administration.

The compositions for administration can include a solution of the antibody dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19th ed., Mack Publishing Company, Easton, Pa. (1995).

Antibodies may be provided in lyophilized form and rehydrated with sterile water before administration, although they are also provided in sterile solutions of known concentration. The antibody solution is then added to an infusion bag containing 0.9% sodium chloride, USP, and in some cases administered at a dosage of from 0.5 to 15 mg/kg of body weight. Considerable experience is available in the art in the administration of antibody drugs, which have been marketed in the U.S. since the approval of RITUXAN® in 1997. *Antibodies can be administered by slow infusion*, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342 and U.S. Pat. No. 5,534,496).

A. Therapeutic Methods

The antibodies, compositions, fusion proteins and immunoconjugates disclosed herein can be administered to slow or inhibit the growth of tumor cells or inhibit the metastasis of tumor cells, such as mesothelioma, prostate cancer, lung cancer, stomach cancer, squamous cell carcinoma, pancreatic cancer, cholangiocarcinoma, breast cancer (such as triple negative breast cancer) or ovarian cancer. In these applications, a therapeutically effective amount of an antibody is administered to a subject in an amount sufficient to inhibit growth, replication or metastasis of cancer cells, or to inhibit a sign or a symptom of the cancer. Suitable subjects may include those diagnosed with a cancer that expresses mesothelin, such as, but not limited to, mesothelioma, prostate cancer, lung cancer, stomach cancer, squamous cell carcinoma, pancreatic cancer, cholangiocarcinoma, triple native breast cancer or ovarian cancer.

In one non-limiting embodiment, provided herein is a method of treating a subject with cancer by selecting a subject having a cancer that expresses mesothelin and administering to the subject a therapeutically effective amount of an antibody, composition, fusion protein or immunoconjugate disclosed herein.

Also provided herein is a method of inhibiting tumor growth or metastasis by selecting a subject having a cancer that expresses mesothelin and administering to the subject a therapeutically effective amount of an antibody, composition, fusion protein or immunoconjugate disclosed herein.

A therapeutically effective amount of a mesothelin-specific antibody, fusion protein, composition or immunoconjugate will depend upon the severity of the disease and the general state of the patient's health. A therapeutically effective amount of the antibody is that which provides either subjective relief of a symptom(s) or an objectively identifiable improvement as noted by the clinician or other qualified observer.

Administration of the antibodies, fusion proteins and immunoconjugates (or compositions thereof) disclosed herein can also be accompanied by administration of other anti-cancer agents or therapeutic treatments (such as surgical resection of a tumor). Any suitable anti-cancer agent can be administered in combination with the antibodies, compositions, fusion proteins and immunoconjugates disclosed herein. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and other antibodies that specifically target cancer cells.

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include *vinca* alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diaminedichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

B. Methods for Diagnosis and Detection

Methods are provided herein for detecting expression of mesothelin in vitro or in vivo. In some cases, mesothelin expression is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a human or non-human primate.

In one embodiment, provided is a method of determining if a subject has cancer by contacting a sample from the subject with a monoclonal antibody disclosed herein; and detecting binding of the antibody to the sample. An increase in binding of the antibody to the sample as compared to binding of the antibody to a control sample identifies the subject as having cancer.

In another embodiment, provided is a method of confirming a diagnosis of cancer in a subject by contacting a sample from a subject diagnosed with cancer with a monoclonal antibody disclosed herein; and detecting binding of the antibody to the sample. An increase in binding of the antibody to the sample as compared to binding of the antibody to a control sample confirms the diagnosis of cancer in the subject.

In some examples of the disclosed methods, the monoclonal antibody is directly labeled.

In some examples, the methods further include contacting a second antibody that specifically binds the monoclonal antibody with the sample; and detecting the binding of the second antibody. An increase in binding of the second antibody to the sample as compared to binding of the second antibody to a control sample detects cancer in the subject or confirms the diagnosis of cancer in the subject.

In some cases, the cancer is mesothelioma, prostate cancer, lung cancer, stomach cancer, squamous cell carcinoma, pancreatic cancer, cholangiocarcinoma, triple negative breast cancer or ovarian cancer, or any other type of cancer that expresses mesothelin.

In some examples, the control sample is a sample from a subject without cancer. In particular examples, the sample is a blood or tissue sample.

In some cases, the antibody that binds (for example specifically binds) mesothelin is directly labeled with a detectable label. In another embodiment, the antibody that binds (for example, specifically binds) mesothelin (the first antibody) is unlabeled and a second antibody or other molecule that can bind the antibody that specifically binds mesothelin is labeled. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}I$, $^{131}I$, $^{35}S$ or $^{3}H$.

In an alternative embodiment, mesothelin can be assayed in a biological sample by a competition immunoassay utilizing mesothelin standards labeled with a detectable substance and an unlabeled antibody that specifically binds mesothelin. In this assay, the biological sample, the labeled mesothelin standards and the antibody that specifically bind mesothelin are combined and the amount of labeled mesothelin standard bound to the unlabeled antibody is determined. The amount of mesothelin in the biological sample is inversely proportional to the amount of labeled mesothelin standard bound to the antibody that specifically binds mesothelin.

The immunoassays and method disclosed herein can be used for a number of purposes. In one embodiment, the antibody that specifically binds mesothelin may be used to detect the production of mesothelin in cells in cell culture. In another embodiment, the antibody can be used to detect the amount of mesothelin in a biological sample, such as a tissue sample, or a blood or serum sample. In some examples, the mesothelin is cell-surface mesothelin. In other examples, the mesothelin is soluble mesothelin (e.g. mesothelin in a cell culture supernatant or soluble mesothelin in a body fluid sample, such as a blood or serum sample).

In one embodiment, a kit is provided for detecting mesothelin in a biological sample, such as a blood sample or tissue sample. For example, to confirm a cancer diagnosis in a subject, a biopsy can be performed to obtain a tissue sample for histological examination. Alternatively, a blood sample can be obtained to detect the presence of soluble mesothelin protein or fragment. Kits for detecting a polypeptide will typically comprise a monoclonal antibody that specifically binds mesothelin, such as any of the antibodies disclosed herein. In some embodiments, an antibody fragment, such as an scFv fragment, a VH domain, or a Fab is included in the kit. In a further embodiment, the antibody is labeled (for example, with a fluorescent, radioactive, or an enzymatic label).

In one embodiment, a kit includes instructional materials disclosing means of use of an antibody that binds mesothelin. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting mesothelin in a biological sample generally includes the steps of contacting the biological sample with an antibody which specifically reacts, under immunologically reactive conditions, to a mesothelin polypeptide. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), ELISA, or immunohistochemical assays. The antibodies can also be used for fluorescence activated cell sorting (FACS). FACS employs a plurality of color channels, low angle and obtuse light-scattering detection channels, and impedance channels, among other more sophisticated levels of detection, to separate or sort cells (see U.S. Pat. No. 5,061,620). Any of the monoclonal antibodies that bind mesothelin, as disclosed herein, can be used in these assays. Thus, the antibodies can be used in a conventional immunoassay, including, without limitation, an ELISA, an RIA, FACS, tissue immunohistochemistry, Western blot or immunoprecipitation.

C. Engineered Cytotoxic T Lymphocytes (CTLs)

The disclosed monoclonal antibodies can also be used to produce CTLs engineered to express chimeric antigen receptors (CARs; also known as chimeric T cell receptors, artificial T cell receptors or chimeric immunoreceptors). Generally, CARs include a binding moiety, an extracellular hinge and spacer element, a transmembrane region and an endodomain that performs signaling functions (Cartellieri et al., *J Biomed Biotechnol* 2010:956304, 2010). In many instances, the binding moiety is an antigen binding fragment of a monoclonal antibody, such as a scFv. Several different endodomains have been used to generate CARs. For example, the endodomain can consist of a signaling chain having an immunoreceptor tyrosine-based activation motif (ITAM), such as CD3ζ or FcεRIγ. In some instances, the endodomain further includes the intracellular portion of at least one additional co-stimulatory domain, such as CD28 and/or CD137.

CTLs expressing CARs can be used to target a specific cell type, such as a tumor cell. Thus, the monoclonal antibodies disclosed herein can be used to engineer CTLs that express a CAR containing an antigen-binding fragment of a mesothelin-specific antibody, thereby targeting the engineered CTLs to mesothelin-expressing tumor cells. Engineered T cells have previously used for adoptive therapy for some types of cancer (see, for example, Park et al., *Mol Ther* 15(4):825-833, 2007). The use of T cells expressing CARs is more universal than standard CTL-based immunotherapy because CTLs expressing CARs are HLA unrestricted and can therefore be used for any patient having a tumor that expressed the target antigen.

Accordingly, provided herein are CARs comprising a mesothelin-specific antibody binding fragment, such as a scFv. Also provided are isolated nucleic acid molecules and vectors encoding the CARs, and host cells, such as CTLs, comprising the nucleic acid molecules or vectors. CTLs expressing CARs comprised of a mesothelin-specific antibody binding fragment can be used for the treatment of cancers that express mesothelin, such as mesothelioma, prostate cancer, lung cancer, stomach cancer, squamous cell carcinoma, pancreatic cancer, cholangiocarcinoma, breast cancer (such as triple negative breast cancer) or ovarian cancer. Thus, provided herein are methods of treating a subject with cancer by selecting a subject having a cancer that expresses mesothelin, and administering to the subject a therapeutically effective amount of the CTLs expressing the mesothelin-targeted CARs.

D. Bispecific Antibodies

Bispecific antibodies are recombinant proteins comprised of antigen-binding fragments of two different monoclonal antibodies. Thus, bispecific antibodies bind two different antigens. Bispecific antibodies can be used for cancer immunotherapy by simultaneously targeting both CTLs (such as a CTL receptor component such as CD3) and a tumor antigen. The mesothelin-specific monoclonal antibodies disclosed herein can be used to generate bispecific antibodies that target both mesothelin and CTLs, thereby providing a means to treat mesothelin-expressing cancers.

Provided herein are bispecific monoclonal antibodies comprising a mesothelin-specific monoclonal antibody, or antigen-binding fragment thereof. In some embodiments, the bispecific monoclonal antibody further comprises a monoclonal antibody, or antigen-binding fragment thereof, that specifically binds a component of the T cell receptor, such as CD3. Also provided are isolated nucleic acid molecules and vectors encoding the bispecific antibodies, and host cells comprising the nucleic acid molecules or vectors. Bispecific antibodies comprising a mesothelin-specific antibody, or antigen-binding fragment thereof, can be used for the treatment of cancers that express mesothelin, such as mesothelioma, prostate cancer, lung cancer, stomach cancer, squamous cell carcinoma, pancreatic cancer, cholangiocarcinoma, breast cancer (such as triple negative breast cancer) or ovarian cancer. Thus, provided herein are methods of treating a subject with cancer by selecting a subject having a cancer that expresses mesothelin, and administering to the subject a therapeutically effective amount of the mesothelin-targeting bispecific antibody.

The following examples are provided to illustrate certain particular features and/or embodiments. These examples should not be construed to limit the disclosure to the particular features or embodiments described.

EXAMPLES

Example 1

Materials and Methods

This example describes the experimental procedures for the studies described in Example 2.

Cell Culture

Human cholangiocarcinoma (CCA) lines (KMBC, Mz-ChA-1 and HuCCT-1), and A431 (epidermal carcinoma), NCI-H226 (mesothelioma), EKVX (human non-small cell lung cancer, or NSCLC), OVCAR-8 (ovarian cancer), and L55 (NSCLC) cells were grown as described (Ho et al., *Int J Cancer* 128:2020-2030, 2011; Yu et al., *J Cancer* 1:141-149, 2010). A431/H9 is a transfected A431 cell line stably expressing human mesothelin (Ho et al., *Clin Cancer Res* 11:3814-3820, 2005). The HEK-293F cell line (Invitrogen, Carlsbad, Calif.) was grown in FreeStyle™ serum-free medium (Invitrogen). All cell lines were passaged only a few times (less than 1 month) after thawing of initial frozen stocks, which were generated right after obtaining cell lines, to reduce total number of passages to less than 15. All cell lines were tested and authenticated by morphology and growth rate and were *Mycoplasma* free.

Screening an Engineered Human Antibody Domain Library

An engineered human ($V_H$) antibody domain library named m81 showed an estimated diversity of $2.5 \times 10^{10}$ (Chen et al., *J Mol Biol* 382:779-789, 2008). The C-terminal mesothelin peptide consisting of 50 amino acids (VQKLLG-PHVEGLKAEERHRPVRDWILRQRQD-DLDTLGLGLQGGIPNGYLV; residues 539-588 of SEQ ID NO: 9) was synthesized (GenScript, Piscataway, N.J.). The full-length human mesothelin protein (MSLN) was prepared as described (Kaneko et al., *J Biol Chem* 284:3739-3749, 2009). The phage library was subjected to four rounds of panning on human mesothelin or the C-terminal mesothelin peptide following a standard lab protocol (Ho et al., *J Biol Chem* 280:607-617, 2005; Ho and Pastan, *Methods Mol Biol* 525:293-308, 2009). Randomly picked clones at the end of each round of panning were analyzed for antigen binding by phage enzyme-linked immunosorbent (ELISA) assays.

Production of a SD1-Human Fc Fusion Protein

The VH region encoding the SD1 human antibody domain fused with human IgGγ1 Fc and FLAG/His tag was PCR amplified with two primers (Forward: GTC ATC ACA ACT T CG ATA TCG CGG TGC AGC GGT GCA GTC TGG GGG AGG CTT GGT A; SEQ ID NO: 10; reverse: GAA GTT GTG ATG ACTCCGGAG CCC TTA TCG TCA TCG TCC TTG TAG TCG CCG TGG; SEQ ID NO: 11). The PCR product was inserted into the EcoRV and BspEI sites (underlined) of the vector, pVRC8400 (Barouch et al., *J Virol* 79:8828-8834, 2005; Ofek et al., *J Virol* 84:2955-2962, 2010). The final plasmid (named pMH148) was transfected into HEK-293F cells and the protein was purified using protein A column (GE healthcare, Piscataway, N.J.). A stable cell line was established by transfecting HEK-293F (Invitrogen) cells with pMH148. The stable line produced the SD1-hFc fusion protein with a high expression level (>70 mg/L) in culture supernatant.

Immunoprecipitation and Western Blot Analysis

Cell lysate (1.5 mg) was incubated with 50 µg of SD1 or an irrelevant human single-domain antibody in 500 µl of RIPA buffer (Cell signaling, Boston, Mass.) and rotated overnight at 4° C. Thirty µl of protein A beads were added (Sigma, St. Louis, Mo.) and rotated at 4° C. for 2 hours. Beads were spun down and washed with RIPA buffer Immune complexes were released from the beads after 5 minutes of boiling in 100 µl of 2× loading buffer. Western blot analysis was performed following a standard lab protocol (Yu et al., *J Cancer* 1:141-149, 2010).

ELISA

Direct ELISA and affinity measurement—the direct binding and affinity of SD1-hFc were evaluated on the ELISA plates coated with mesothelin peptide, human mesothelin, or mouse mesothelin (mMSLN) following the procedures described previously (Kaneko et al., *J Biol Chem* 284:3739-3749, 2009).

Competition ELISA—various amounts of mesothelin peptide, an irrelevant 50 amino acid peptide, the HN1 human mAb or the SS1P immunotoxin were mixed with 5 µg/ml of SD1-hFc and incubated at room temperature for 1 hour. The mixture was then transferred to an ELISA plate coated with 5 µg/ml of human mesothelin protein and incubated at room temperature for an additional hour following the procedure described above.

Flow Cytometry

To determine the binding of the SD1 antibody to cell surface associated mesothelin, flow cytometry analysis was performed according to a standard protocol (Yu et al., *J Cancer* 1:141-149, 2010). The average number of mesothelin sites per cell was measured on a FACSCalibur (BD Biosciences, San Jose, Calif.) using BD Quantibrite™ PE beads (BD Biosciences). C1q and anti-mesothelin binding assays were conducted following an established protocol (Pawluczkowycz et al., *J Immunol* 183:749-758, 2009; Li et al., *Cancer Res* 68:2400-2408, 2008). Briefly, A431/H9 or NCI-H226 cells were suspended at $1 \times 10^6$ cells/ml and incubated with different concentration of SD1-hFc, control human IgG or the HN1 human IgG on ice for 1 hour. After washing, the cells were incubated with 20 µg/ml purified C1q (Complement Technologies, Tyler, Tenn.) at 37 C.° for 0.5 hour. The cells were washed again and then incubated with FITC-labeled sheep anti-human C1q mAb (AbD Serotec, Raleigh, N.C.) for 0.5 hour on ice. At the end of the incubation, cells were washed and analyzed using a FACSCalibur.

ADCC and CDC

ADCC assay was performed using an LDH detection kit (Roche, Mannheim, Germany) according to a standard protocol (Ho et al., *Int J Cancer* 128:2020-2030, 2011). CDC activity of SD1-hFc was also measured by LDH-releasing assay. Briefly, cells were incubated with SD1-hFc for 1 hour in DMEM culture medium in a 5% $CO_2$ incubator at 37° C., followed by addition of normal human serum (20% vol/vol) or freshly drawn mouse serum (30% vol/vol) as a source of complement. Normal human sera were provided by the Department of Transfusion Medicine, NIH Clinical Center (Bethesda, Md.). After an additional incubation for 4 hours at 37° C., cell lysis was determined by measuring the amount of LDH released into the culture supernatant. Maximum LDH release was determined by lysis in 1% Triton X-100. Percentage of specific lysis was calculated according to the following formula: % lysis=[experimental release−spontaneous release]/[maximum release−spontaneous release]×100.

Xenograft Anti-Tumor Testing in Mice

Tumor experiments evaluating SD1-hFc were conducted using A431/H9 xenografts in nude mice following a well-established NCI protocol (Hassan et al., *Cancer Immun* 7:20, 2007). Four to six week old female athymic nude mice were housed in micro-isolation cages during the course of the experiment. Three million A431/H9 cells were inoculated subcutaneously into the right flank of the mice. Tumor dimensions were determined using calipers and the tumor volume ($mm^3$) was calculated by the formula: length×(width)$^2$×0.5. Treatment was initiated when tumors reached approximately 70 $mm^3$ in size. The different treatment regimens included: PBS and SD1-hFc (50 mg/kg) via i.v. injection on days 7, 9, 11, 14, 17, 20 after tumor inoculation. Mice were sacrificed when tumors reached over 1000 $mm^3$.

Production of a Recombinant Immunotoxin

The SD1 antibody domain from selected phagemids was PCR amplified using two primers (forward: GTC ATC ACA ACT TCCATATGC AGG TGC AGC TGG TGC AGT CT, SEQ ID NO: 12; and reverse: GAA GTT GTG ATG AC AAGCTTT GGC CGC ACT TGA GGA GAC GGT GAC CAG GGT TC; SEQ ID NO: 13) that introduced NdeI and Hind-III restriction sites (underlined). The products of the reaction were cloned into pRB98. The final expression plasmid (named pMH149) was used for the production of recombinant immunotoxins as previously described (Pastan and Ho, "Recombinant immunotoxins for Treating Cancer," in *Antibody Engineering*, Volume II, New York: Springer; 2010, pages 127-146).

Cell Proliferation Inhibition Assay

Cell growth inhibition was measured by WST-8 assays as previously described (Ho et al., *Int J Cancer* 128:2020-2302, 2011; Ho et al., *J Biol Chem* 280:607-617, 2005).

Example 2

A Human Single-Domain Antibody Elicits Potent Anti-Tumor Activity by Targeting an Epitope in Mesothelin Close to the Cancer Cell Surface This example describes the identification and characterization of a human single-domain antibody specific for a C-terminal epitope of human mesothelin.

Discovery and Production of the SD1 Human Antibody

To find a new anti-mesothelin mAb targeting a site close to the cell surface, a C-terminal mesothelin peptide was designed for screening a library of small-size binders (VHs). The human mesothelin (MSLN) gene encodes a precursor protein of 622 amino acids (GenBank accession no. AY743922). Upon translocation into the endoplasmic reticulum, the N-terminal signal peptide (residues: 1-33) and the C-terminal GPI anchor addition signal (predicted cleavage site: Ser598) are removed and the latter is replaced with a GPI anchor. Using the big-PI Predictor program, the GPI cleavage site was predicted as Ser598. Initially the intent was to make a 50-amino acid peptide (residues 549-598) corresponding to the predicted C-terminal end, however, synthesis failed after aggregation issues possibly due to the hydrophobic property of the peptide. A new peptide was designed (residues 539-588 of SEQ ID NO: 9; VQKLLGPHVEGLKAEERHRPVRD-WILRQRQDDLDTLGLGLQGGIPNGYLV), 10 amino acids away from the GPI cleavage site of mesothelin (FIG. 1A). The new peptide was used for phage panning with an engineered human antibody domain phage display library (Chen et al., *J Mol Biol* 382:779-789, 2008) (Table 1).

Figure 1D:
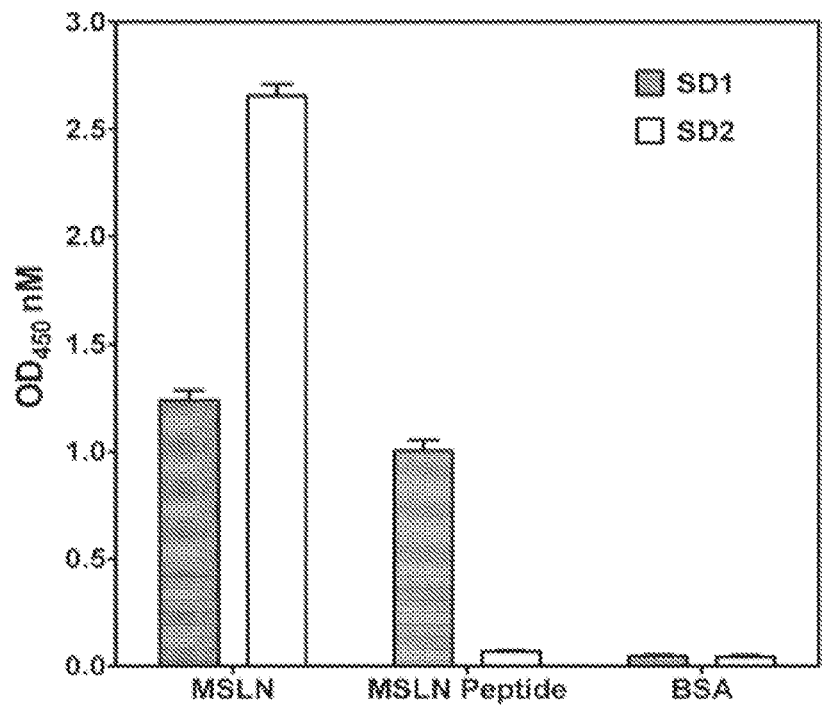

After the fourth round of phage panning, phage titer was significantly increased (FIG. 1B) and more than 95% of clones were peptide binders. Phage clone SD1 was selected for further analysis because it bound not only the peptide but also full-length mesothelin (FIG. 1C). In comparison, the same single-domain antibody phage library was screened on human mesothelin, but only clone SD2 was enriched and specific for full-length human mesothelin, but not the peptide (FIG. 1D). It seems unlikely to obtain mAbs that recognize the C-terminal end of mesothelin if screened on full-length proteins either by hybridoma (Onda et al., *Clin Cancer Res* 11:5840-5846, 2005) or phage display technology.

TABLE 1

Phage panning

| Round | Phages input (pfu) | Phage output (pfu) | Enrichment (folds, phage output compared to the last round) | Total Enrichment (folds, phage output compared to the 1st round) |
|---|---|---|---|---|
| 1 | $3.6 \times 10^{11}$ | $9.8 \times 10^{4}$ | | 1 |
| 2 | $2.4 \times 10^{11}$ | $2.6 \times 10^{4}$ | 0.3 | 0.3 |
| 3 | $2.0 \times 10^{11}$ | $2.4 \times 10^{6}$ | 92 | 24 |
| 4 | $3.0 \times 10^{11}$ | $1.4 \times 10^{8}$ | 58 | 1429 |

Phage titer after each round of panning was shown as plaque forming units (pfu).

Figure 2A:
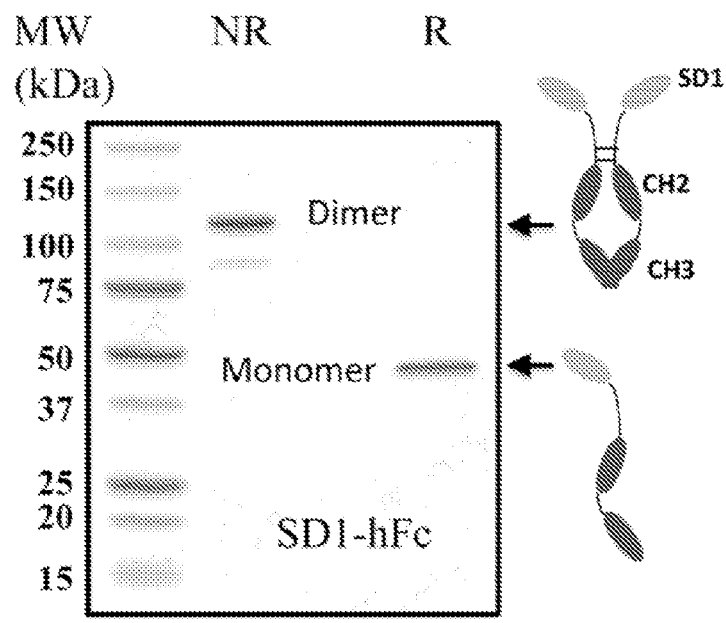
FIGS. 2A-2B: Production and analysis of the SD1 human Fc fusion protein.

To investigate SD1 as a potential therapeutic, it was converted into a clinically relevant molecule: a human Fc (hFc) fusion protein (FIG. 2A). The SD1-hFc human protein was generated by fusing the human VH into the $CH_2$ and $CH_3$ in the constant region of human IgG heavy chain γ1. To make large-scale production of the SD1-hFc fusion protein, a stable cell line was established with a high expression level (>70 mg/L) in the culture supernatant of HEK-293F cells. SD1-hFc is an antibody-like dimeric molecule (without the light chain) and is approximately 100 kDa estimated on SDS-PAGE under non-reducing condition. Therefore, the SD1 human antibody domain was successfully isolated against the C-terminal end of mesothelin by phage display, and a human Fc fusion (SD1-hFc) was produced based on the SD1 VH for potential clinical applications.

The SD1 Human Antibody Binds Cancer Cell Surface-Associated Mesothelin

Figure 2B:
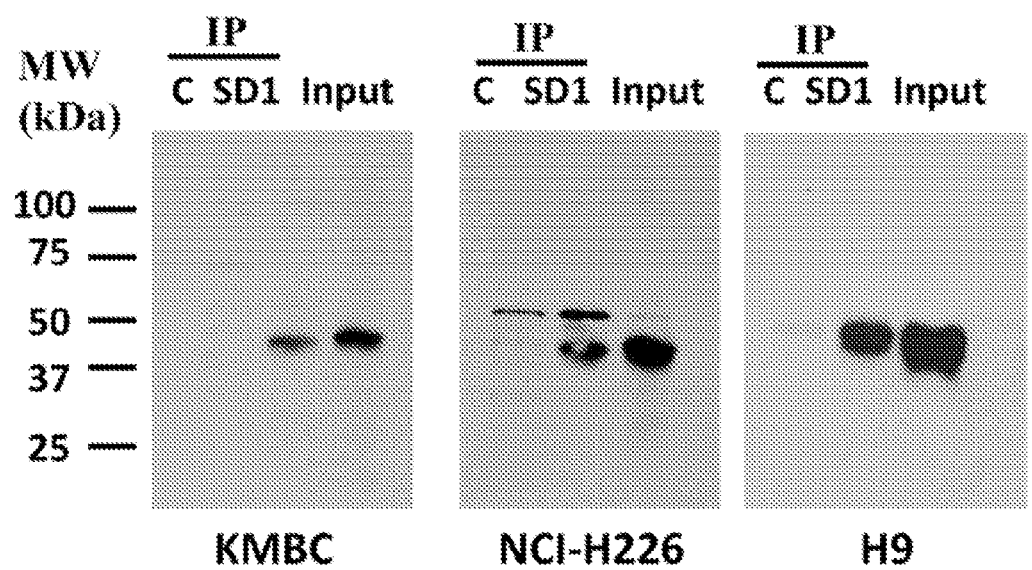
Figure 3B:
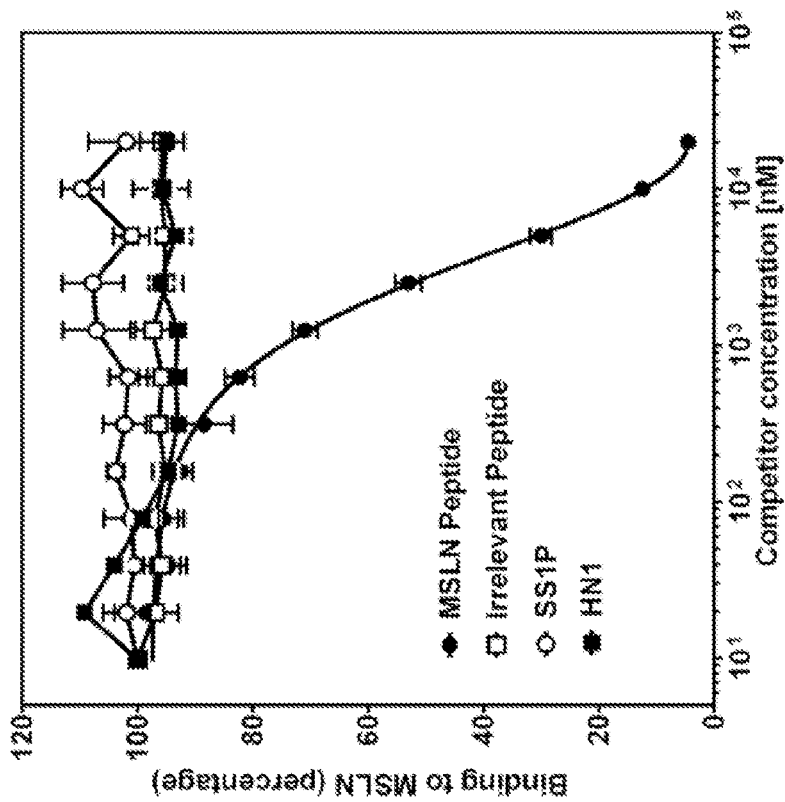
FIGS. 3A-3D: Binding properties of SD1-hFc.
Figure 3A:
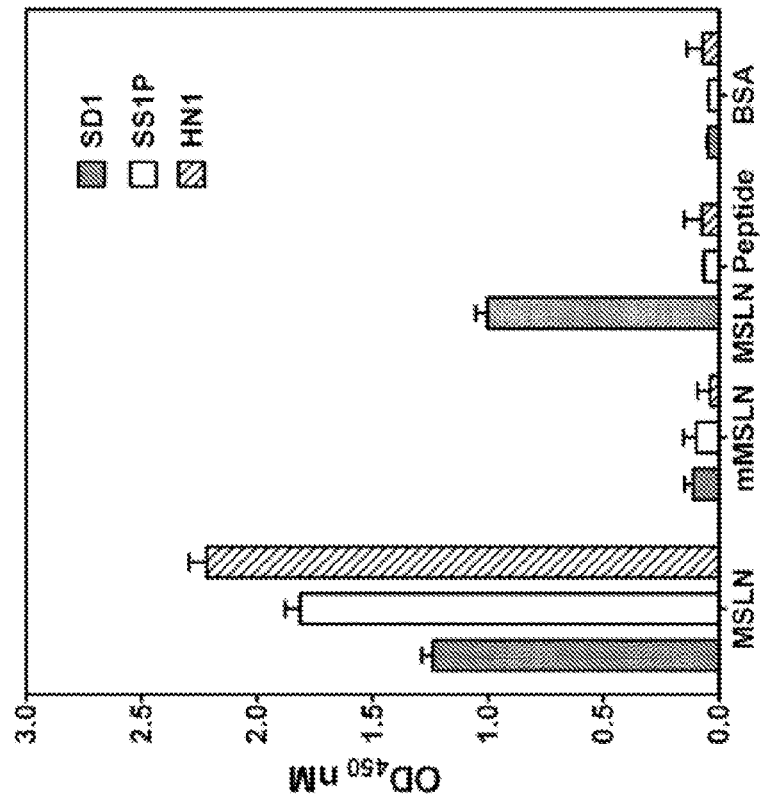
Figure 3D:
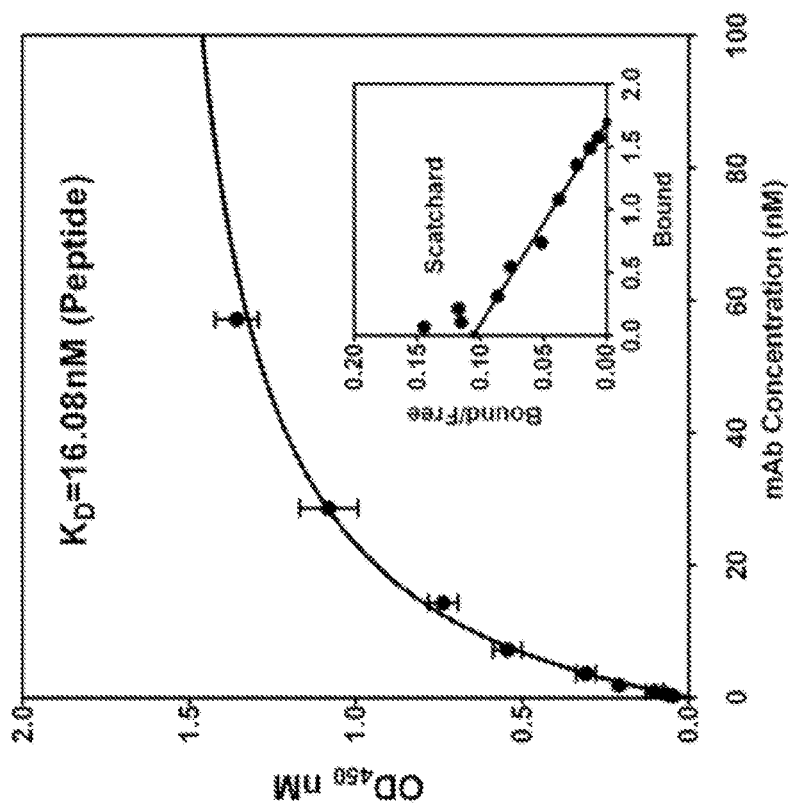
Figure 3C:
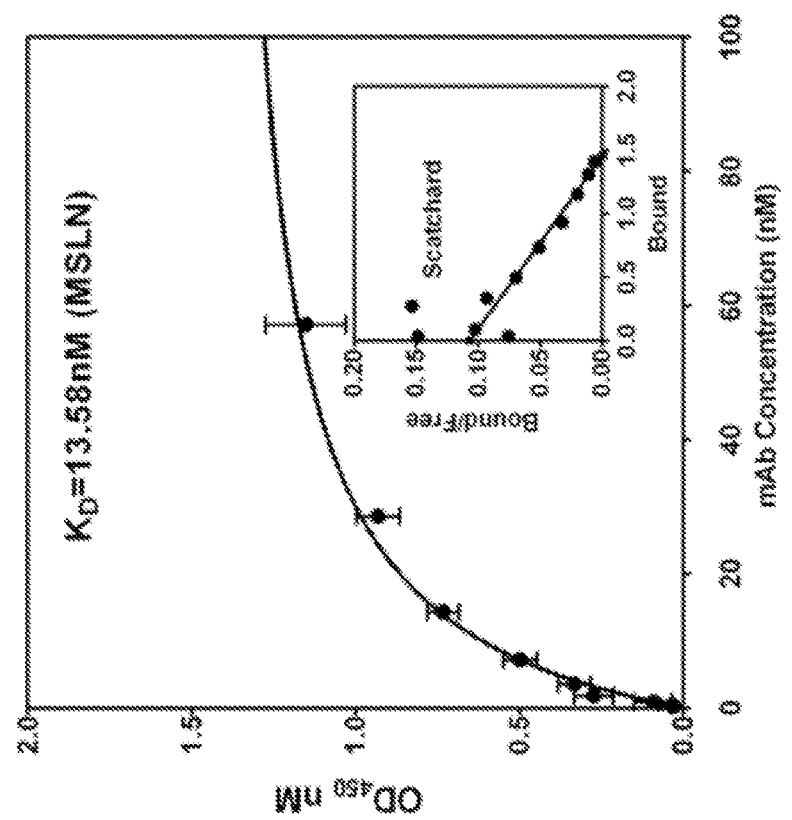

To analyze the binding properties of the SD1 antibody to mesothelin protein in cancer cells, SD1-hFc or an irrelevant human VH single-domain hFc fusion protein as a control was used to perform Western blot and pull-down assays using cancer cell lysates. Initial Western blot analysis of various cancer cell lysates using SD1-hFc could not detect a mesothelin band under reducing condition even in high mesothelin-expressing cell lines such as A431/H9 and NCI-H226, indicating that SD1-hFc did not recognize denatured mesothelin protein. By conducting pull-down assays to detect endogenous mesothelin proteins in solution, as shown in FIG. 2B, the SD1-hFc protein successfully pulled down mature mesothelin protein from three different cancer cell lines (A431/H9, NCI-H226 and KMBC). NCI-H226 and KMBC are native human cancer cell lines. A431/H9 was an engineered A431 line overexpressing mesothelin on the cell surface (Ho et al., *Clin Cancer Res* 11:3814-3820, 2005). The molecular weight of mature mesothelin (~40 kDa) was consistent with previous studies (Yu et al., *J Cancer* 1:141-149, 2010; Ho et al., *Clin Cancer Res* 13:1571-1575, 2007). In ELISA assays, the SD1-hFc protein bound both full-length human mesothelin protein and mesothelin peptide (FIG. 3A), and did not bind full-length mouse mesothelin protein, BSA or other irrelevant proteins. As expected, SS1P and HN1 bind only full-length human mesothelin, not the C-terminal peptide.

To evaluate whether SD1-hFc recognizes the C-terminal end, we pre-incubated SD1-hFc, HN1, or SS1P with mesothelin peptide (residues 539-588) and tested binding of the antibody-peptide mixture to human mesothelin coated on an ELISA plate. Competition ELISAs (FIG. 3B) showed that the C-terminal peptide blocked the binding of SD1-hFc, not SS1P or HN1, to full-length human mesothelin, indicating SD1-hFc bound the C-terminal sequence and that SD1 binding to mesothelin could not be competed by SS1P and HN1. The kinetics of SD1 binding was also measured using full-length mesothelin protein and the C-terminal peptide. SD1-hFc binds to human mesothelin protein with dissociate equilibrium ($K_D$) of 13.59 nM, and to the peptide with a $K_D$ of 16.08 nM. The equilibrium constants and Scatchard plots were determined by using Prism (version 3.02) for Windows (GraphPad software, San Diego, Calif.) (Kaneko et al., *J Biol Chem* 284:3739-3749, 2009).

Figure 4:
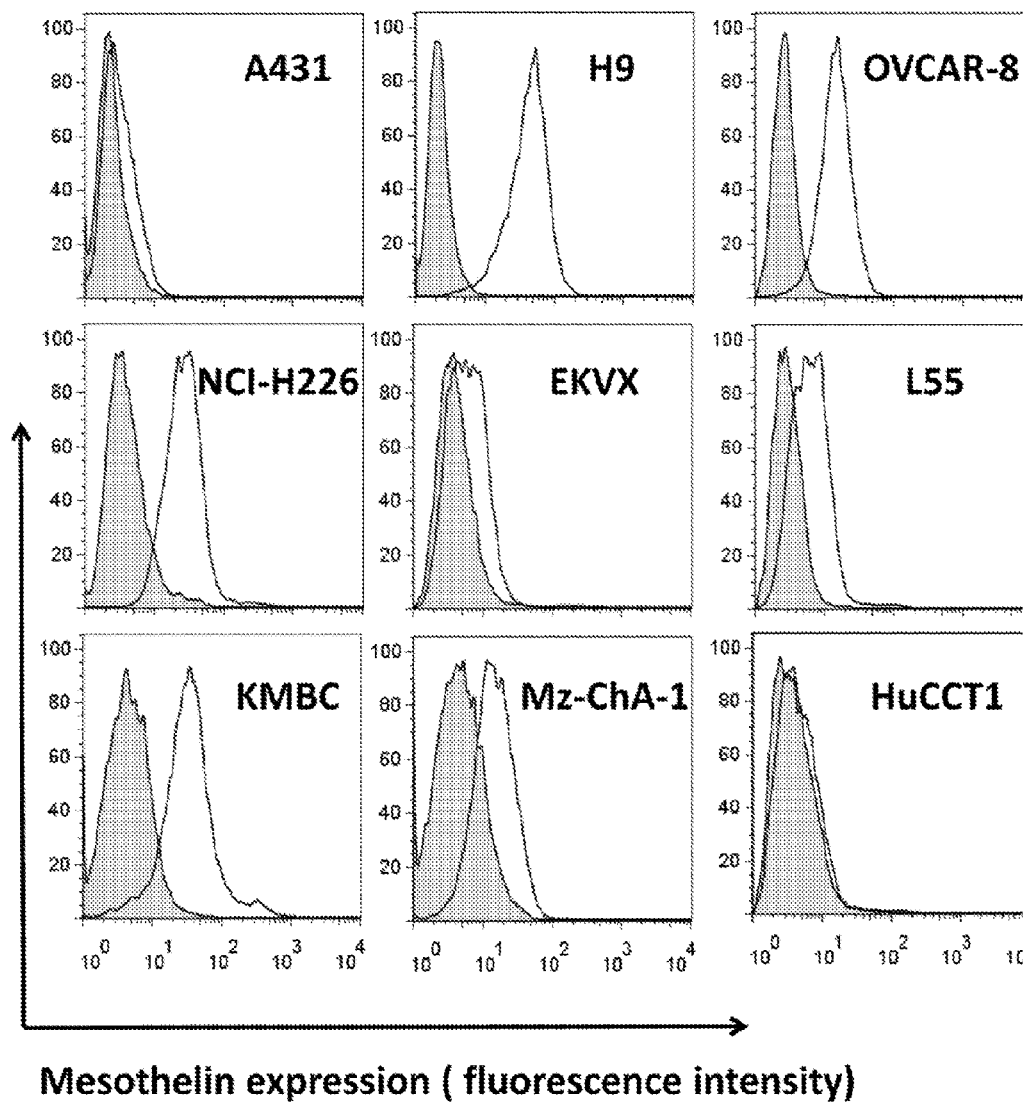
FIG. 4: Flow cytometry analysis of the SD1-hFc protein on mesothelin-expressing and control cancer cells. SD1-hFc bound the stable mesothelin cDNA transfected A431/H9 cell line and not the A431 cell line. The antibody also bound three out of four human cancer cell lines tested in the present study. OVCAR8: ovarian cancer; NCI-H226: mesothelioma; EKVX and L55: NSCLC; KMBC, Mz-ChA-1 and HuCCT1: cholangiocarcinoma.

To analyze whether SD1 is suitable for cancer therapy, it was determined whether SD1-hFc binds native mesothelin molecules on human tumor cells. Flow cytometric analysis was performed on a panel of mesothelin-expressing cancer cells and the average number of mesothelin sites per cell was experimentally measured using the QuantiBRITE fluorescence quantitation system (Table 2). The SD1-hFc protein binds A431/H9, but not A431, indicating that SD1 binding on cell surface-associated mesothelin is highly specific (FIG. 4). The binding of SD1-hFc on a panel of native human tumor cell lines was also tested. Previous studies have shown that mesothelin is highly expressed in malignant mesothelioma, ovarian cancer (Chang et al., *Cancer Res* 52:181-186, 1992), lung adenocarcinoma (Ho et al., *Clin Cancer Res* 13:1571-1575, 2007) and cholangiocarcinoma (Yu et al., *J Cancer* 1:141-149, 2010). In the present study, it was found that SD1-hFc strongly bound human ovarian cancer (OVCAR-8), mesothelioma (NCI-H226), human NSCLC cell lines (EKVX and L55), and cholangiocarcinoma cell lines (KMBC and Mz-ChA-1); it did not bind to cholangiocarcinoma cells, HuCCT1, which is a mesothelin-negative line (Yu et al., *J Cancer* 1:141-149, 2010). Taken together, these results show that the SD1 human antibody recognizes a conformational epitope of native mesothelin close to the cancer cell surface and binds cell-surface associated native mesothelin proteins with high affinity and excellent specificity.

TABLE 2

The number of mesothelin sites per cell on cancer cell lines

| Cell line | Tumor type | Mesothelin sites/cell | SD1(VH)-PE38 (nM) | BL22 (nM) |
|---|---|---|---|---|
| A431 | Epidermoid carcinoma | Negative* | >100 | >100 |
| H9 | Forced expression of mesothelin in A431 | $7 \times 10^5$ | 0.46 | >100 |
| NCI-H226 | Mesothelioma | $5 \times 10^5$ | 1.25 | >100 |
| OVCAR-8 | Ovarian cancer | $5 \times 10^4$ | 3.84 | >100 |
| KMBC | Cholangiocarcinoma | $1 \times 10^5$ | 1.62 | >100 |
| Mz-ChA-1 | Cholangiocarcinoma | $3 \times 10^4$ | 2.2 | >100 |
| HuCCT-1 | Cholangiocarcinoma | Negative* | >100 | >100 |

*Absence of mesothelin expression was validated by Western blot.

Anti-Tumor Activity of SD1-hFc: CDC and ADCC

Figure 5A:
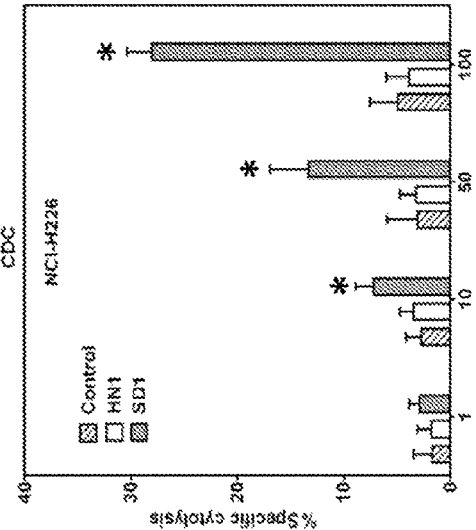
Figure 5B:
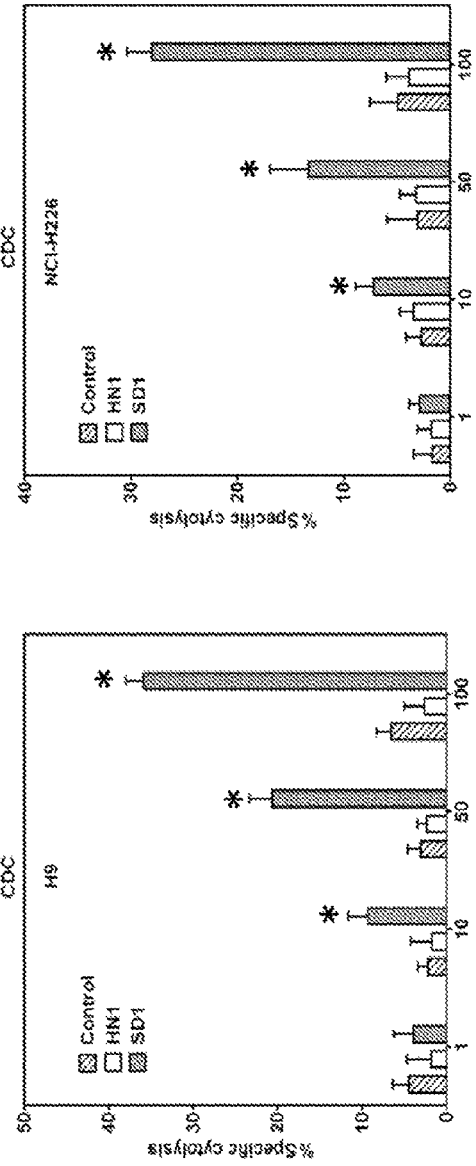

To evaluate the anti-tumor activity of SD1-hFc against cancer cells, the cytotoxic activity in A431/H9 and NCI-H226 cell models in the presence of human serum as a source of complement was tested. SD1-hFc exerted potent CDC activity by killing 40% of A431/H9 (FIG. 5A) and more than 30% of NCI-H226 mesothelioma cell lines (FIG. 5B) and showed no activity on the mesothelin-negative A431 cell line. An irrelevant control antibody showed no activity at the same concentrations. This is an important observation because MORAb-009, a chimeric antibody that is currently being evaluated in clinical trials, shows no significant CDC activity against tumor cells (Hassan et al., *Cancer Immun* 7:20, 2007). It has been suggested that mesothelin-bound MORAb-009 may be too far from the cell surface for the complement membrane attack complex (MAC) to be effective. By targeting a mesothelin epitope close to the cell surface, mesothelin-bound SD1-hFc may cause effective complement MAC on the cancer cell surface.

Figure 5C:
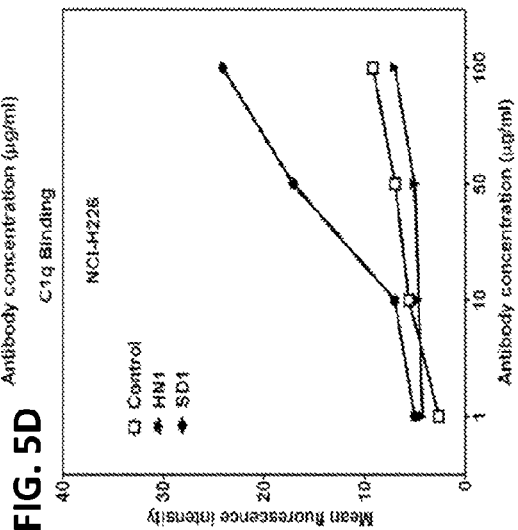
Figure 5D:
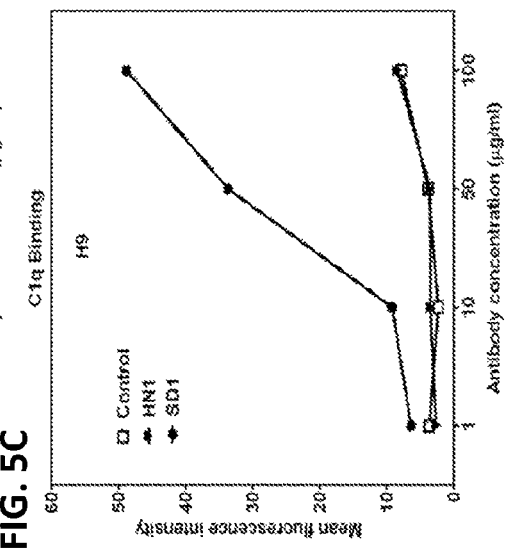

To analyze the role of complement in the anti-tumor activity of SD1-hFc, flow cytometry was used to determine C1q binding to cancer cells reacted with anti-mesothelin human mAbs following a well-established protocol for characterization of rituximab, ofatumumab and other anti-CD20 therapeutic mAbs (Pawluczkowycz et al., *J Immunol* 183:749-758, 2009; Li et al., *Cancer Res* 68:2400-2408, 2008). It was previously shown that like MORAb-009, the HN1 human mAb specific for Region I of cell surface mesothelin (far from the cell surface), did not exhibit any CDC activity against mesothelin-expressing cancer cells (Ho et al., *Int J Cancer* 128:2020-2030, 2011). As shown in FIGS. 5C and 5D, the C1q complement bound to A431/H9 or NCI-H226 cells in the presence of SD1-hFc. However, no C1q binding was found in the presence of HN1 or a control hFc fusion protein. Moreover, the binding of C1q to cancer cells is associated with the cell binding of SD1-hFc in a dose-response manner. These results demonstrate that the C-terminal end binder SD1-hFc, not the N-terminal end binder HN1, can recruit C1q to the mesothelin-expressing cancer cell surface.

In addition to CDC activity, ADCC activity of SD1-hFc against tumor cells was tested. High levels of cytotoxicity were found using SD1-hFc with human peripheral blood mononuclear cells (PBMC) at different concentrations. SD1 exhibited significant ADCC activity against both A431/H9 cells (FIG. 5E) and NCI-H226 mesothelioma cells (FIG. 5F). No activity was found on mesothelin-negative A431 cells. ADCC activity of SD1-hFc against tumor cells using purified human NK cells was also tested. Human NK cells were incubated with A431/H9 or NCI-H226 target cells (at E:T ratios of 5:1, 10:1 and 20:1) and 50 µg/ml of SD1-hFc. Again, SD1 exhibited significant ADCC activity against both A431/H9 and NCI-H226 cells at all E:T ratios (FIGS. 5G-5H).

Taken together, these results suggest that the SD1-hFc protein has strong CDC and ADCC anti-tumor activity against mesothelin-expressing tumor cells in vitro.

Anti-Tumor Activity in Mice

Figure 6A:
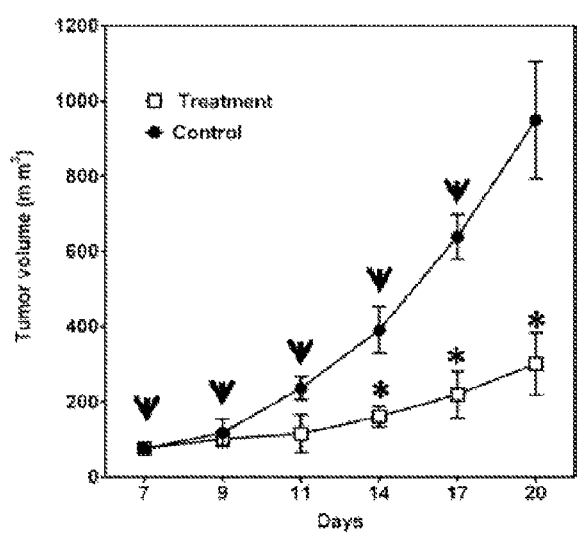
FIGS. 6A-6D: Strong anti-tumor effect of SD1-hFc on tumor growth.

To evaluate the anti-tumor activity of SD1-hFc in vivo, immunodeficient mice bearing tumor xenografts were used following an established protocol used to evaluate MORAb-009 in preclinical studies (Hassan et al., *Cancer Immun* 7:20, 2007). From day 7, athymic nude mice bearing A431/H9 tumors were treated with 50 mg/kg of SD1-hFc (FIG. 6A). The number of mesothelin sites in A431/H9 is comparable to that of malignant mesothelioma cells endogenously expressing mesothelin and their implantation in mice consistently results in aggressive tumor growth. Twenty days after inoculation of tumor cells, the average tumor size in mice treated with SD1-hFc alone was significantly reduced (average 300 mm$^3$) compared to the control group (average 1000 mm$^3$) These results demonstrate that SD1-hFc is very active as a single agent. Using the same protocol, MORAb-009 as a single agent only moderately induced tumor growth inhibition in mice (Hassan et al., *Cancer Immun* 7:20, 2007). ADCC and CDC are important mechanisms of tumor cell killing mediated by antibodies used in cancer therapy. SD1-hFc causes both ADCC and CDC against tumor cells, but MORAb-009 induces only ADCC, not CDC. Therefore, it is believed that CDC plays an important role in its potent tumor growth inhibition in mice.

Figure 6B:
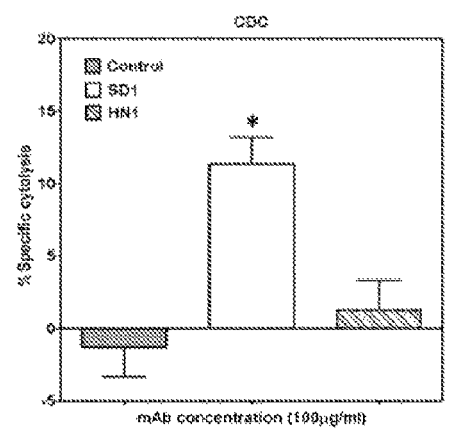
Figure 6C:
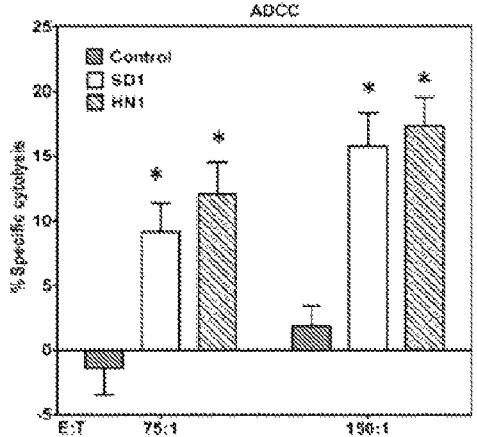
Figure 6D:
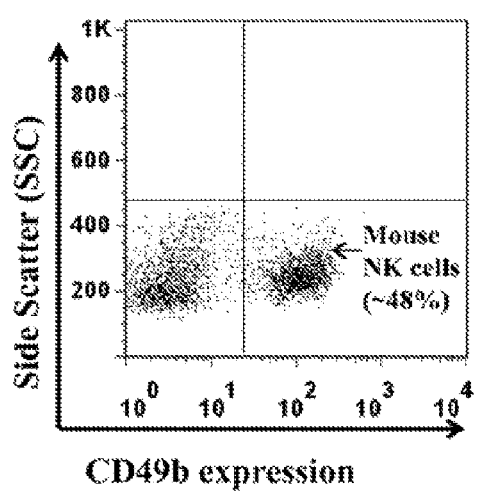

To evaluate SD1-induced CDC in mice, CDC activity was examined using mouse sera. SD1-hFc killed 11% of A431/H9 cells in the presence of 30% mouse serum freshly drawn from nude mice (FIG. 6B), indicating that mouse complements were 10-fold less active than human complements (FIG. 5) for SD1-hFc. It is consistent with previous studies showing that for antibodies with a human Fc, mouse complements are less active than human complements (Di Gaetano et al., *J Immunol* 171:1581-1587, 2003). HN1 did not induce significant levels of CDC. ADCC induced by SD1 and HN1 was also evaluated. Both antibodies were capable of inducing significant levels of ADCC (FIG. 6C). The purity of mouse NK cells is shown in FIG. 6D.

In conclusion, it was shown that SD1-hFc induces potent tumor growth inhibition in mice and CDC appears to be a major underlying mechanism.

DISCUSSION

Disclosed herein is the identification of SD1, an engineered antibody domain that recognizes an epitope at the C-terminal end of mesothelin, by phage display technology. This epitope does not overlap with epitopes of any current therapeutic antibodies (SS1P/MORAb-009 and HN1) that are in preclinical and clinical development for mesothelin-targeted therapy.

SD1 shows strong in vitro and in vivo anti-tumor activity. In in vitro assays, the SD1-hFc protein shows strong CDC activity against mesothelin-expressing cancer cells. In in vivo mouse testing, the SD1-hFc protein exhibits potent tumor growth inhibition. The results disclosed herein indicate that SD1 represents a new class of anti-mesothelin mAbs and can be used as a therapeutic antibody for mesothelin-targeted therapy.

The SD1 domain was isolated by phage panning on a C-terminal 50-residue peptide of mesothelin. It was demonstrated that the antibody binds native mesothelin proteins in cancer cells by flow cytometry and pull-down assays. It does not bind denatured mesothelin proteins on Western blot, indicating the SD1 domain binds a conformational epitope of mesothelin close to the cancer cell surface. This region has never been accessed by any known anti-mesothelin antibodies (including SS1P/MORAb-009 and HN1). It is believed that it is an important strategy to develop an antibody targeting this region. CDC is one of the most powerful cell killing mechanisms of therapeutic antibodies against tumors, but may require an antibody binding site close to the cell membrane (Pawluczkowycz et al., *J Immunol* 183:749-758, 2009). The present data demonstrate that CDC triggered by SD1-hFc depends on the specific new epitope because HN1 (specific for the N-terminus of mesothelin, Region I, far from the cell surface) does not exhibit CDC activity and cannot recruit C1q to cancer cells. Moreover, almost all of the existing mesothelin antibodies (e.g., MORAb-009/amatuximab, SS1P, HN1) recognize Region I. However, it was previously shown that abundant mucin MUC16/CA125 also bound Region I of mesothelin on cancer cells (Kaneko et al., *J Biol Chem* 284: 3739-3749, 2009) and might compete with antibody binding. SD1 does not compete with MUC16/CA125 binding on mesothelin; therefore, the binding and activity of SD1 to tumor cells is unlikely to be neutralized by MUC16/CA125.

The in vivo animal testing using a xenograft tumor model in nude mice showed potent anti-tumor activity of SD1-hFc. Using a similar protocol, the anti-tumor effect of the MORAb-009 mouse/human chimeric mAb alone showed only modest anti-tumor activity, most likely because MORAb-009 does not cause significant CDC activity against tumor cells (Hassan et al., *Cancer Immun* 7:20, 2007). To further evaluate SD1-hFc in a tumor microenvironment, human tumor xenografts were generated in mice and it was shown that SD1-hFc was indeed very active in vivo.

Figure 7A:
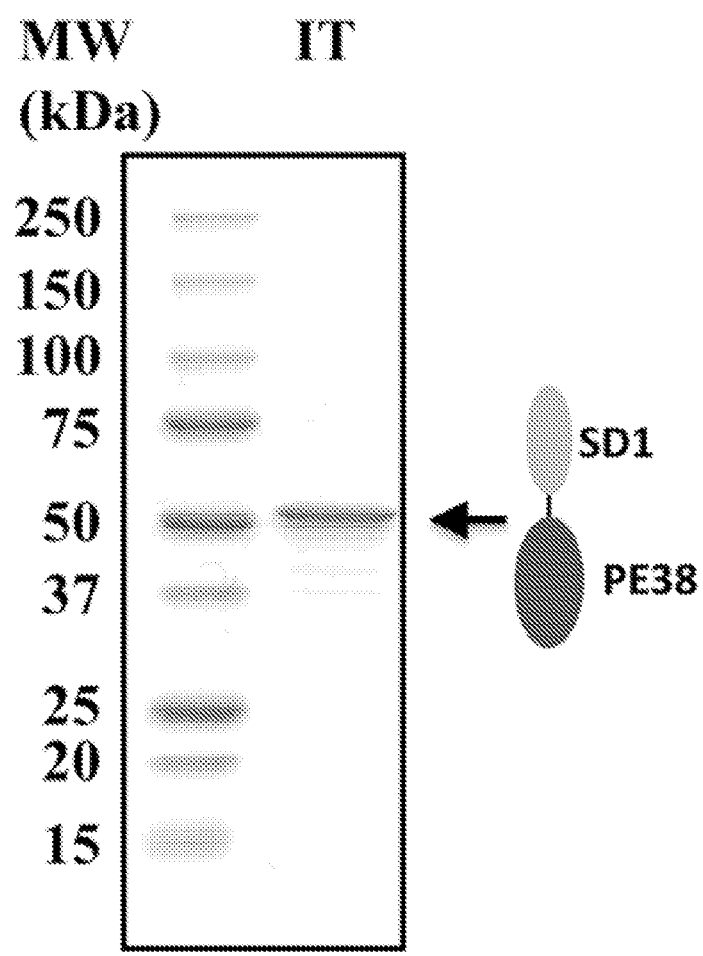
FIGS. 7A-7B: Production and analysis of the SD1-based recombinant immunotoxin.
Figure 7B:
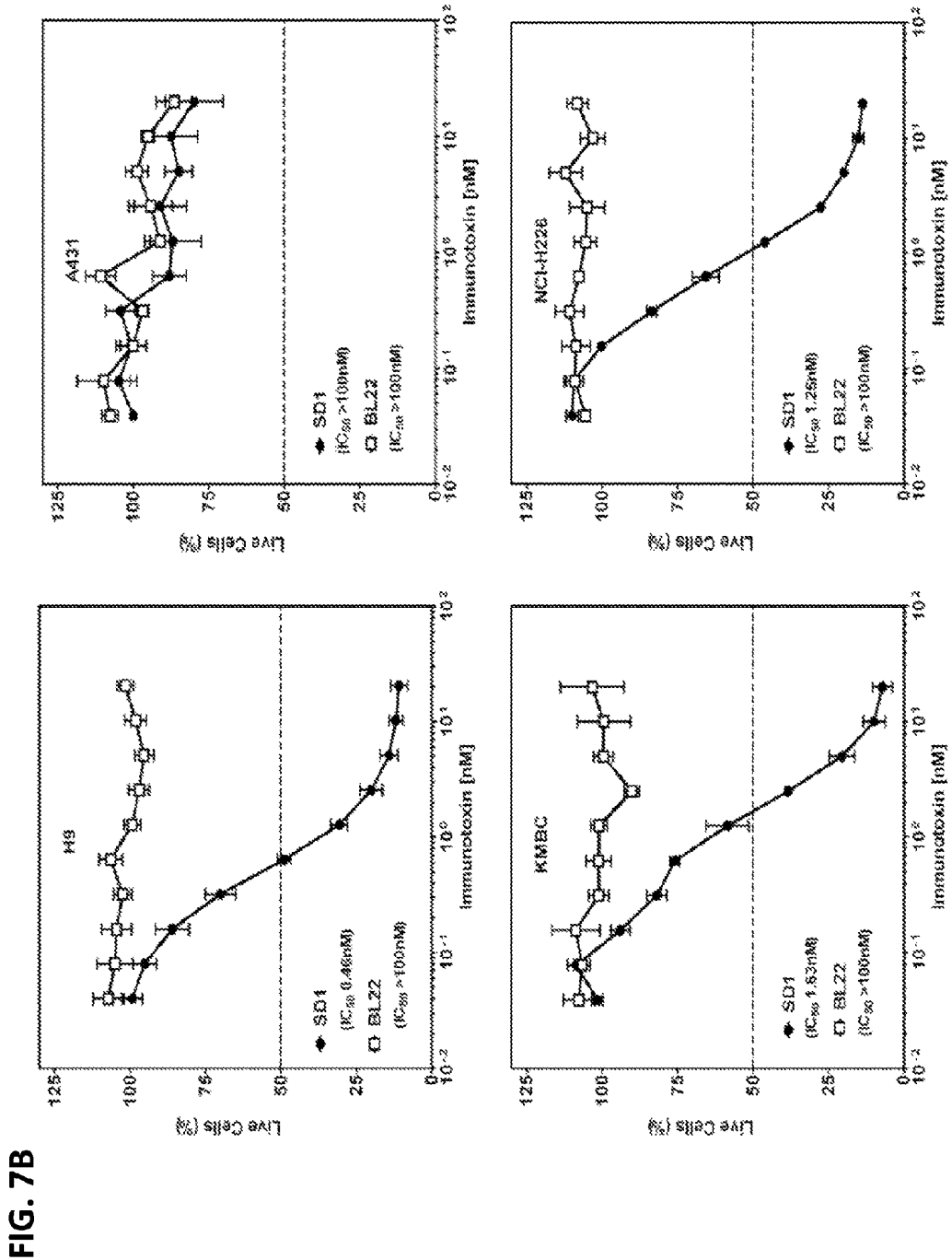

Naturally occurring single-domain antibodies such as camelid VHHs and shark VNARs have been suggested as a novel class of therapeutics for cancer immunotherapy. Due to the likelihood of immunogenicity in humans, these animal antibodies may not be used directly for some clinical applications. Therefore, human single-domain VHs are attractive candidates for cancer therapy. However, human VHs are typically prone to aggregation (Arbabi-Ghahroudi et al., *Methods Mol Biol* 502:341-364, 2009). In the present study, the SD1 VH was fused to the $CH_2$ and $CH_3$ of human IgGγ1 and to produce SD1-hFc as a dimeric IgG-like protein in mammalian HEK-293F cells. A recombinant immunotoxin based on SD1 was also produced, which could inhibit proliferation of mesothelin-positive tumor cells in a dose-dependent manner (Table 2 and FIGS. 7A-7B). All the recombinant proteins were properly folded for in vitro and in vivo assays.

In summary, the first human single-domain antibody against mesothelin-expressing tumors was generated and shown to have potent anti-tumor activity in vitro and in vivo by targeting an epitope close the cancer cell surface via CDC and ADCC. Such a binding site has not been accessed by any known anti-mesothelin antibodies currently in preclinical or clinical studies.

Example 3

Mesothelin-Specific Monoclonal Antibodies for Detecting Cancer in a Subject or Confirming the Diagnosis of Cancer in a Subject This example describes the use of mesothelin-specific monoclonal antibodies, such as the monoclonal antibodies disclosed herein (for example, SD1 or SD2, or a monoclonal antibody comprising the CDR sequences of SD1 or SD2) for the detection of cancer in a subject. This example further describes the use of these antibodies to confirm the diagnosis of cancer in a subject.

A blood sample is obtained from the patient diagnosed with, or suspected of having a mesothelin-positive cancer (i.e., a cancer that overexpresses mesothelin, such as mesothelioma, prostate cancer, lung cancer, stomach cancer, squamous cell carcinoma, pancreatic cancer, cholangiocarcinoma, triple negative breast cancer or ovarian cancer). A blood sample taken from a patient that does not have cancer can be used as a control. An ELISA is performed to detect the presence of soluble mesothelin in the blood sample. Proteins present in the blood samples (the patient sample and control sample) are immobilized on a solid support, such as a 96-well plate, according to methods well known in the art (see, for example, Robinson et al., *Lancet* 362:1612-1616, 2003). Following immobilization, mesothelin-specific monoclonal antibody directly labeled with a fluorescent marker is applied to the protein-immobilized plate. The plate is washed in an appropriate buffer, such as PBS, to remove any unbound antibody and to minimize non-specific binding of antibody. Fluorescence can be detected using a fluorometric plate reader according to standard methods. An increase in fluorescence intensity of the patient sample, relative to the control sample, indicates the anti-mesothelin antibody specifically bound proteins from the blood sample, thus detecting the presence of mesothelin protein in the sample. Detection of mesothelin protein in the patient sample indicates the patient has a mesothelin-positive cancer, or confirms diagnosis of cancer in the subject.

Example 4

Mesothelin-Specific Monoclonal Antibodies for the Treatment of Cancer

This example describes the use of mesothelin-specific monoclonal antibodies, such as the monoclonal antibodies disclosed herein (for example, SD1 or SD2, or a monoclonal antibody comprising the CDR sequences of SD1 or SD2), for the treatment of cancers that exhibit overexpression of mesothelin (referred to herein as a "mesothelin-positive" cancer), including, but not limited to mesothelioma, prostate cancer, lung cancer, stomach cancer, squamous cell carcinoma, pancreatic cancer, cholangiocarcinoma, triple negative breast cancer or ovarian cancer. Patients diagnosed with a mesothelin-positive cancer can be treated according to standard procedures in the art (see, for example, Hassan et al., *Proc. Am. Soc. Clin. Oncol.* 21:29a, 2002; Kreiman et al., *Proc. Am. Soc. Clint Oncol.* 21:22b, 2002).

In one example, patients diagnosed with a mesothelin-positive cancer are administered an immunoconjugate comprising a mesothelin-specific monoclonal antibody linked to *Pseudomonas* exotoxin (PE). Preparation of PE immunoconjugates has been described (see, for example, U.S. Pat. No. 7,081,518 and U.S. Patent Application Publication No. 2005/

0214304). In another example, patients diagnosed with a mesothelin-positive cancer are administered SD1 or an SD1-hFc fusion protein, which is capable of inducing both CDC and ADCC and can thereby mediate tumor cell killing without being linked to a toxin.

In some patients, SD1, SD1-hFc or the immunoconjugate is administered by intravenous bolus injection every other day for a total of three to six doses. In other patients, the SD1, SD1-hFc or immunoconjugate is administered by continuous intravenous infusion over the course of ten days. The dose of SD1, SD1-hFc or immunoconjugate administered to a patient varies depending on the weight and gender of the patient, and mode and time course of administration. Following treatment, patients are evaluated for cancer progression (including tumor growth and metastasis) and other clinical signs of illness.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. An isolated human variable heavy (VH) single domain monoclonal antibody that specifically binds human mesothelin, wherein the antibody comprises a complementarity determining region (CDR) 1, a CDR2 and a CDR3 respectively set forth as:
 (i) amino acid residues 26-35, 51-58 and 97-103 of SEQ ID NO: 2;
 (ii) amino acid residues 31-35, 51-66 and 99-102 of SEQ ID NO: 2;
 (iii) amino acid residues 26-33, 51-57 and 96-111 of SEQ ID NO: 15; or
 (iv) amino acid residues 31-35, 50-65 and 99-106 of SEQ ID NO: 15.

2. The isolated human VH single domain monoclonal antibody of claim 1, wherein the amino acid sequence of the antibody is at least 90% or at least 95% identical to SEQ ID NO: 2 or SEQ ID NO: 15.

3. The isolated human VH single domain monoclonal antibody of claim 1, wherein the amino acid sequence of the antibody comprises SEQ ID NO: 2 or SEQ ID NO: 15.

4. The isolated human VH single domain monoclonal antibody of claim 1, wherein the antibody is chimeric or synthetic.

5. The isolated human VH single domain monoclonal antibody of claim 1, wherein the antibody is labeled.

6. The isolated human VH single domain monoclonal antibody of claim 5, wherein the label is a fluorescent, enzymatic, or radioactive label.

7. An isolated immunoconjugate comprising the human VH single domain monoclonal antibody of claim 1 and an effector molecule.

8. The isolated immunoconjugate of claim 7, wherein the effector molecule is a toxin.

9. The isolated immunoconjugate of claim 8, wherein the toxin is *Pseudomonas* exotoxin or a variant thereof.

10. The isolated immunoconjugate of claim 9, wherein the *Pseudomonas* exotoxin or a variant thereof comprises the amino acid sequence of any one of SEQ ID NOs: 3-8.

11. A fusion protein comprising the human VH single domain monoclonal antibody of claim 1 and a heterologous protein.

12. The fusion protein of claim 11, wherein the heterologous protein is a human Fc protein.

13. A composition comprising a therapeutically effective amount of the human VH single domain monoclonal antibody of claim 1 in a pharmaceutically acceptable carrier.

14. A method of treating a mesothelin-expressing cancer in a subject, comprising selecting a subject having a mesothelin-expressing cancer and administering to the subject a therapeutically effective amount of the human VH single domain monoclonal antibody of claim 1, wherein the antibody comprises a CDR1, a CDR2 and a CDR3 respectively set forth as:
 (i) amino acid residues 26-35, 51-58 and 97-103 of SEQ ID NO: 2; or
 (ii) amino acid resides 31-35, 51-66 and 99-102 or SEQ ID NO: 2,
 wherein the antibody is fused to a human Fc protein or to a toxin, thereby treating the mesothelin-expressing cancer.

15. A method of inhibiting tumor growth or metastasis of a mesothelin-expressing tumor in a subject, comprising selecting a subject having a mesothelin-expressing tumor and administering to the subject a therapeutically effective amount of the human VH single domain monoclonal antibody of claim 1, wherein the antibody comprises a CDR1, a CDR2 and a CDR3 respectively set forth as:
 (i) amino acid resides 26-35, 51-58 and 97-103 of SEQ ID NO: 2; or
 (ii) amino acid residues 31-35, 51-66 and 99-102 of SEQ ID NO: 2,
 wherein the antibody is fused to a human Fc protein or to a toxin, thereby inhibiting tumor growth or metastasis.

16. A method of detecting mesothelin in a biological sample, comprising:
 contacting the sample with the human VH single domain monoclonal antibody of claim 1; and
 detecting binding of the antibody to the sample,
 wherein an increase in binding of the antibody to the sample as compared to binding of the antibody to a control sample detects mesothelin in the biological sample.

17. The method of claim 14, wherein the cancer is mesothelioma, prostate cancer, lung cancer, stomach cancer, squamous cell carcinoma, pancreatic cancer, cholangiocarcinoma, triple negative breast cancer or ovarian cancer.

18. An isolated nucleic acid molecule encoding the human VH single domain monoclonal antibody of claim 1.

19. The isolated nucleic acid molecule of claim 18, wherein the nucleotide sequence encoding the antibody comprises SEQ ID NO: 1 or SEQ ID NO: 14.

20. The isolated nucleic acid molecule of claim 18, operably linked to a promoter.

21. An expression vector comprising the isolated nucleic acid molecule of claim 20.

22. An isolated host cell transformed with the expression vector of claim 21.

23. The fusion protein of claim 12, wherein the human Fc protein comprises human IgGγ1 Fc.

24. A chimeric antigen receptor (CAR) comprising the human VH single domain monoclonal antibody of claim 1.

25. A bispecific antibody comprising the human VH single domain monoclonal antibody of claim 1.

26. An isolated immunoconjugate comprising the human VH single domain monoclonal antibody of claim 1 and a therapeutic agent.

27. The isolated immunoconjugate of claim 26, wherein the therapeutic agent comprises a drug.

28. The method of claim 15, wherein the cancer is mesothelioma, prostate cancer, lung cancer, stomach cancer, squamous cell carcinoma, pancreatic cancer, cholangiocarcinoma, triple negative breast cancer or ovarian cancer.

\* \* \* \* \*

SEQUENCE LISTING

```
<160> NUMBER OF SEQ ID NOS: 15

<210> SEQ ID NO 1
<211> LENGTH: 339
<212> TYPE: DNA
<213> ORGANISM: Artificial Sequence
<220> FEATURE:
<223> OTHER INFORMATION: Synthetic oligonucleotide

<400> SEQUENCE: 1
caggtgcagc tggtgcagtc tgggggaggc ttggtacagc ctggagggtc cctgagactc    60
tcctgtgcag cctctgattt cgatttcgct gcttatgaaa tgagctgggt ccgccaggct   120
ccaggacaag gccttgagtg ggtggcaatt atatcacatg atggaatcga taaatactac   180
acagactccg tgaagggccg attcaccatc tccagagaca attccaagaa cacgctgtat   240
ctgcaaatga acaccctgag agccgaggac acagccacgt attactgttt aaggcttggt   300
gctgtaggcc agggaaccct ggtcaccgtc tcctcaagt                          339

<210> SEQ ID NO 2
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 2

Gln Val Gln Leu Val Gln Ser Gly Gly Gly Leu Val Gln Pro Gly Gly
1               5                   10                  15

Ser Leu Arg Leu Ser Cys Ala Ala Ser Asp Phe Asp Phe Ala Ala Tyr
            20                  25                  30

Glu Met Ser Trp Val Arg Gln Ala Pro Gly Gln Gly Leu Glu Trp Val
        35                  40                  45

Ala Ile Ile Ser His Asp Gly Ile Asp Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Thr Tyr Tyr Cys
                85                  90                  95

Leu Arg Leu Gly Ala Val Gly Gln Gly Thr Leu Val Thr Val Ser Ser
            100                 105                 110

Ser

<210> SEQ ID NO 3
<211> LENGTH: 613
<212> TYPE: PRT
<213> ORGANISM: Pseudomonas aeruginosa
```

```
<400> SEQUENCE: 3

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
                115                 120                 125

Met Ser Pro Ile Tyr Thr Ile Glu Met Gly Asp Glu Leu Leu Ala Lys
130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
                180                 185                 190

Gly Lys Val Leu Cys Leu Leu Asp Pro Leu Asp Gly Val Tyr Asn Tyr
            195                 200                 205

Leu Ala Gln Gln Arg Cys Asn Leu Asp Asp Thr Trp Glu Gly Lys Ile
210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
            275                 280                 285

Tyr Pro Val Gln Arg Leu Val Ala Leu Tyr Leu Ala Ala Arg Leu Ser
290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Val Arg
            340                 345                 350

Gln Gly Thr Gly Asn Asp Glu Ala Gly Ala Ala Asn Ala Asp Val Val
                355                 360                 365

Ser Leu Thr Cys Pro Val Ala Ala Gly Glu Cys Ala Gly Pro Ala Asp
            370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415
```

```
Trp Thr Val Glu Arg Leu Leu Gln Ala His Arg Gln Leu Glu Arg
            420                 425                 430

Gly Tyr Val Phe Val Gly Tyr His Gly Thr Phe Leu Glu Ala Ala Gln
        435                 440                 445

Ser Ile Val Phe Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610

<210> SEQ ID NO 4
<211> LENGTH: 345
<212> TYPE: PRT
<213> ORGANISM: Artificial Sequence
<220> FEATURE:
<223> OTHER INFORMATION: Synthetic polypeptide

<400> SEQUENCE: 4

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg Asn Ala Leu
    50                  55                  60

Ala Ser Pro Gly Ser Gly Asp Leu Gly Glu Ala Ile Arg Glu Gln
65                  70                  75                  80

Pro Glu Gln Ala Arg Leu Ala Leu Thr Leu Ala Ala Glu Ser Glu
                85                  90                  95

Arg Phe Val Arg Gln Gly Thr Gly Asn Asp Glu Ala Gly Ala Ala Asn
            100                 105                 110

Gly Pro Ala Asp Ser Gly Asp Ala Leu Leu Glu Arg Asn Tyr Pro Thr
        115                 120                 125

Gly Ala Glu Phe Leu Gly Asp Gly Gly Asp Val Ser Phe Ser Thr Arg
    130                 135                 140

Gly Thr Gln Asn Trp Thr Val Glu Arg Leu Leu Gln Ala His Arg Gln
145                 150                 155                 160
```

```
Leu Glu Glu Arg Gly Tyr Val Phe Val Gly Tyr His Gly Thr Phe Leu
            165                 170                 175
Glu Ala Ala Gln Ser Ile Val Phe Gly Gly Val Arg Ala Arg Ser Gln
        180                 185                 190
Asp Leu Asp Ala Ile Trp Arg Gly Phe Tyr Ile Ala Gly Asp Pro Ala
    195                 200                 205
Leu Ala Tyr Gly Tyr Ala Gln Asp Gln Glu Pro Asp Ala Arg Gly Arg
210                 215                 220
Ile Arg Asn Gly Ala Leu Leu Arg Val Tyr Val Pro Arg Ser Ser Leu
225                 230                 235                 240
Pro Gly Phe Tyr Arg Thr Ser Leu Thr Leu Ala Ala Pro Glu Ala Ala
                245                 250                 255
Gly Glu Val Glu Arg Leu Ile Gly His Pro Leu Pro Leu Arg Leu Asp
            260                 265                 270
Ala Ile Thr Gly Pro Glu Glu Gly Gly Arg Leu Glu Thr Ile Leu
        275                 280                 285
Gly Trp Pro Leu Ala Glu Arg Thr Val Val Ile Pro Ser Ala Ile Pro
    290                 295                 300
Thr Asp Pro Arg Asn Val Gly Asp Leu Asp Pro Ser Ser Ile Pro
305                 310                 315                 320
Asp Lys Glu Gln Ala Ile Ser Ala Leu Pro Asp Tyr Ala Ser Gln Pro
                325                 330                 335
Gly Lys Pro Pro Arg Glu Asp Leu Lys
            340                 345

<210> SEQ ID NO 5
<211> LENGTH: 230
<212> TYPE: PRT
<213> ORGANISM: Artificial Sequence
<220> FEATURE:
<223> OTHER INFORMATION: Synthetic polypeptide

<400> SEQUENCE: 5

Arg His Arg Gln Pro Arg Gly Trp Glu Gln Leu Pro Thr Gly Ala Glu
1               5                   10                  15
Phe Leu Gly Asp Gly Gly Asp Val Ser Phe Ser Thr Arg Gly Thr Gln
            20                  25                  30
Asn Trp Thr Val Glu Arg Leu Leu Gln Ala His Arg Gln Leu Glu Glu
        35                  40                  45
Arg Gly Tyr Val Phe Val Gly Tyr His Gly Thr Phe Leu Glu Ala Ala
    50                  55                  60
Gln Ser Ile Val Phe Gly Gly Val Arg Ala Arg Ser Gln Asp Leu Asp
65                  70                  75                  80
Ala Ile Trp Arg Gly Phe Tyr Ile Ala Gly Asp Pro Ala Leu Ala Tyr
                85                  90                  95
Gly Tyr Ala Gln Asp Gln Glu Pro Asp Ala Arg Gly Arg Ile Arg Asn
            100                 105                 110
Gly Ala Leu Leu Arg Val Tyr Val Pro Arg Ser Ser Leu Pro Gly Phe
        115                 120                 125
Tyr Arg Thr Ser Leu Thr Leu Ala Ala Pro Glu Ala Ala Gly Glu Val
    130                 135                 140
Glu Arg Leu Ile Gly His Pro Leu Pro Leu Arg Leu Asp Ala Ile Thr
145                 150                 155                 160
Gly Pro Glu Glu Glu Gly Gly Arg Leu Glu Thr Ile Leu Gly Trp Pro
                165                 170                 175
```

```
Leu Ala Glu Arg Thr Val Val Ile Pro Ser Ala Ile Pro Thr Asp Pro
                180                 185                 190

Arg Asn Val Gly Gly Asp Leu Asp Pro Ser Ser Ile Pro Asp Lys Glu
            195                 200                 205

Gln Ala Ile Ser Ala Leu Pro Asp Tyr Ala Ser Gln Pro Gly Lys Pro
        210                 215                 220

Pro Arg Glu Asp Leu Lys
225                 230

<210> SEQ ID NO 6
<211> LENGTH: 230
<212> TYPE: PRT
<213> ORGANISM: Artificial Sequence
<220> FEATURE:
<223> OTHER INFORMATION: Synthetic polypeptide

<400> SEQUENCE: 6

Arg His Arg Gln Pro Arg Gly Trp Glu Gln Leu Pro Thr Gly Ala Glu
1               5                   10                  15

Phe Leu Gly Asp Gly Gly Asp Val Ser Phe Ser Thr Arg Gly Thr Gln
                20                  25                  30

Asn Trp Thr Val Glu Arg Leu Leu Gln Ala His Arg Gln Leu Glu Glu
            35                  40                  45

Gly Gly Tyr Val Phe Val Gly Tyr His Gly Thr Phe Leu Glu Ala Ala
        50                  55                  60

Gln Ser Ile Val Phe Gly Gly Val Arg Ala Arg Ser Gln Asp Leu Asp
65                  70                  75                  80

Ala Ile Trp Ala Gly Phe Tyr Ile Ala Gly Asp Pro Ala Leu Ala Tyr
                85                  90                  95

Gly Tyr Ala Gln Asp Gln Glu Pro Asp Ala Ala Gly Arg Ile Arg Asn
            100                 105                 110

Gly Ala Leu Leu Arg Val Tyr Val Pro Arg Ser Ser Leu Pro Gly Phe
        115                 120                 125

Tyr Ala Thr Ser Leu Thr Leu Ala Ala Pro Glu Ala Ala Gly Glu Val
130                 135                 140

Glu Arg Leu Ile Gly His Pro Leu Pro Leu Arg Leu Asp Ala Ile Thr
145                 150                 155                 160

Gly Pro Glu Glu Ser Gly Gly Arg Leu Glu Thr Ile Leu Gly Trp Pro
                165                 170                 175

Leu Ala Glu Arg Thr Val Val Ile Pro Ser Ala Ile Pro Thr Asp Pro
            180                 185                 190

Arg Asn Val Gly Gly Asp Leu Asp Pro Ser Ser Ile Pro Asp Ser Glu
        195                 200                 205

Gln Ala Ile Ser Ala Leu Pro Asp Tyr Ala Ser Gln Pro Gly Lys Pro
    210                 215                 220

Pro Arg Glu Asp Leu Lys
225                 230

<210> SEQ ID NO 7
<211> LENGTH: 230
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (23)..(23)
<223> OTHER INFORMATION: Xaa = Gly, Ser or Ala
```

```
<220> FEATURE:
<221> NAME/KEY: MISC_FEATURE
<222> LOCATION: (49)..(49)
<223> OTHER INFORMATION: Xaa = Gly, Ser or Ala
<220> FEATURE:
<221> NAME/KEY: MISC_FEATURE
<222> LOCATION: (84)..(84)
<223> OTHER INFORMATION: Xaa = Gly, Ser or Ala
<220> FEATURE:
<221> NAME/KEY: MISC_FEATURE
<222> LOCATION: (107)..(107)
<223> OTHER INFORMATION: Xaa = Gly, Ser or Ala
<220> FEATURE:
<221> NAME/KEY: MISC_FEATURE
<222> LOCATION: (130)..(130)
<223> OTHER INFORMATION: Xaa = Gly, Ser or Ala
<220> FEATURE:
<221> NAME/KEY: MISC_FEATURE
<222> LOCATION: (165)..(165)
<223> OTHER INFORMATION: Xaa = Gly, Ser or Ala
<220> FEATURE:
<221> NAME/KEY: MISC_FEATURE
<222> LOCATION: (207)..(207)
<223> OTHER INFORMATION: Xaa = Gly, Ser or Ala
<220> FEATURE:
<221> NAME/KEY: MISC_FEATURE
<222> LOCATION: (209)..(209)
<223> OTHER INFORMATION: Xaa = Gly, Ser or Ala

<400> SEQUENCE: 7

Arg His Arg Gln Pro Arg Gly Trp Glu Gln Leu Pro Thr Gly Ala Glu
1               5                   10                  15

Phe Leu Gly Asp Gly Gly Xaa Val Ser Phe Ser Thr Arg Gly Thr Gln
            20                  25                  30

Asn Trp Thr Val Glu Arg Leu Leu Gln Ala His Arg Gln Leu Glu Glu
        35                  40                  45

Xaa Gly Tyr Val Phe Val Gly Tyr His Gly Thr Phe Leu Glu Ala Ala
    50                  55                  60

Gln Ser Ile Val Phe Gly Gly Val Arg Ala Arg Ser Gln Asp Leu Asp
65                  70                  75                  80

Ala Ile Trp Xaa Gly Phe Tyr Ile Ala Gly Asp Pro Ala Leu Ala Tyr
                85                  90                  95

Gly Tyr Ala Gln Asp Gln Glu Pro Asp Ala Xaa Gly Arg Ile Arg Asn
            100                 105                 110

Gly Ala Leu Leu Arg Val Tyr Val Pro Arg Ser Ser Leu Pro Gly Phe
        115                 120                 125

Tyr Xaa Thr Ser Leu Thr Leu Ala Ala Pro Glu Ala Ala Gly Glu Val
    130                 135                 140

Glu Arg Leu Ile Gly His Pro Leu Pro Leu Arg Leu Asp Ala Ile Thr
145                 150                 155                 160

Gly Pro Glu Glu Xaa Gly Gly Arg Leu Glu Thr Ile Leu Gly Trp Pro
                165                 170                 175

Leu Ala Glu Arg Thr Val Val Ile Pro Ser Ala Ile Pro Thr Asp Pro
            180                 185                 190

Arg Asn Val Gly Gly Asp Leu Asp Pro Ser Ser Ile Pro Asp Xaa Glu
        195                 200                 205

Xaa Ala Ile Ser Ala Leu Pro Asp Tyr Ala Ser Gln Pro Gly Lys Pro
    210                 215                 220

Pro Arg Glu Asp Leu Lys
225                 230
```

```
<210> SEQ ID NO 8
<211> LENGTH: 230
<212> TYPE: PRT
<213> ORGANISM: Artificial Sequence
<220> FEATURE:
<223> OTHER INFORMATION: Synthetic polypeptide

<400> SEQUENCE: 8

Arg His Arg Gln Pro Arg Gly Trp Glu Gln Leu Pro Thr Gly Ala Glu
1               5                   10                  15

Phe Leu Gly Asp Gly Gly Ala Val Ser Phe Ser Thr Arg Gly Thr Gln
                20                  25                  30

Asn Trp Thr Val Glu Arg Leu Leu Gln Ala His Arg Gln Leu Glu Glu
            35                  40                  45

Gly Gly Tyr Val Phe Val Gly Tyr His Gly Thr Phe Leu Glu Ala Ala
        50                  55                  60

Gln Ser Ile Val Phe Gly Gly Val Arg Ala Arg Ser Gln Asp Leu Asp
65                  70                  75                  80

Ala Ile Trp Ala Gly Phe Tyr Ile Ala Gly Asp Pro Ala Leu Ala Tyr
                85                  90                  95

Gly Tyr Ala Gln Asp Gln Glu Pro Asp Ala Ala Gly Arg Ile Arg Asn
            100                 105                 110

Gly Ala Leu Leu Arg Val Tyr Val Pro Arg Ser Ser Leu Pro Gly Phe
        115                 120                 125

Tyr Ala Thr Ser Leu Thr Leu Ala Ala Pro Glu Ala Ala Gly Glu Val
    130                 135                 140

Glu Arg Leu Ile Gly His Pro Leu Pro Leu Arg Leu Asp Ala Ile Thr
145                 150                 155                 160

Gly Pro Glu Glu Ser Gly Gly Arg Leu Glu Thr Ile Leu Gly Trp Pro
                165                 170                 175

Leu Ala Glu Arg Thr Val Val Ile Pro Ser Ala Ile Pro Thr Asp Pro
            180                 185                 190

Arg Asn Val Gly Gly Asp Leu Asp Pro Ser Ser Ile Pro Asp Ser Glu
        195                 200                 205

Ala Ala Ile Ser Ala Leu Pro Asp Tyr Ala Ser Gln Pro Gly Lys Pro
    210                 215                 220

Pro Arg Glu Asp Leu Lys
225                 230

<210> SEQ ID NO 9
<211> LENGTH: 622
<212> TYPE: PRT
<213> ORGANISM: Homo sapiens

<400> SEQUENCE: 9

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
                20                  25                  30

Pro Ser Arg Thr Leu Ala Gly Glu Thr Gly Gln Glu Ala Ala Pro Leu
            35                  40                  45

Asp Gly Val Leu Ala Asn Pro Pro Asn Ile Ser Ser Leu Ser Pro Arg
        50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95
```

```
Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Pro Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
        500                 505                 510
```

| | | | | | | | | | | | | |
|---|---|---|---|---|---|---|---|---|---|---|---|---|
|Gln|Gln|Asn|Val|Ser|Met|Asp|Leu|Ala|Thr|Phe|Met|Lys|Leu|Arg|Thr|
| | | 515 | | | | 520 | | | | 525 | | |

Asp Ala Val Leu Pro Leu Thr Val Ala Glu Val Gln Lys Leu Leu Gly
     530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
             580                 585                 590

Met Gln Glu Ala Leu Ser Gly Thr Pro Cys Leu Leu Gly Pro Gly Pro
         595                 600                 605

Val Leu Thr Val Leu Ala Leu Leu Ala Ser Thr Leu Ala
     610                 615                 620

<210> SEQ ID NO 10
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 10
gtcatcacaa cttcgatatc gcggtgcagc ggtgcagtct gggggaggct tggta        55

<210> SEQ ID NO 11
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 11
gaagttgtga tgactccgga gcccttatcg tcatcgtcct tgtagtcgcc gtgg         54

<210> SEQ ID NO 12
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 12
gtcatcacaa cttccatatg caggtgcagc tggtgcagtc t                      41

<210> SEQ ID NO 13
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 13
gaagttgtga tgacaagctt tggccgcact tgaggagacg gtgaccaggg ttc         53

<210> SEQ ID NO 14
<211> LENGTH: 363
<212> TYPE: DNA
<213> ORGANISM: Artificial Sequence
<220> FEATURE:
<223> OTHER INFORMATION: Synthetic polynucleotide

```
<400> SEQUENCE: 14
caggtgcagc tggtgcagtc tggggggaggc ttggtacagc ctggagggtc cctgagactc      60
tcctgtgcag cctctgattt cgctttcgat gattatgaaa tgagctgggt ccgccaggct     120
ccaggaaagg cccttgagtg gattggggac atcaatcata gtggaaccac catctacaac     180
ccgtccctca agagtcgagt caccatctcc agagacaatt ccaagaacac gctgtatctg     240
caaatgaaca ccctgagagc cgaggacaca gccatatatt actgtgcgag acctcactac     300
ggtgactact ctgatgcttt tgatatctgg ggccaaggga caatggtcac cgtctcctca     360
agt                                                                   363

<210> SEQ ID NO 15
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 15

Gln Val Gln Leu Val Gln Ser Gly Gly Gly Leu Val Gln Pro Gly Gly
1               5                   10                  15

Ser Leu Arg Leu Ser Cys Ala Ala Ser Asp Phe Ala Phe Asp Asp Tyr
            20                  25                  30

Glu Met Ser Trp Val Arg Gln Ala Pro Gly Lys Ala Leu Glu Trp Ile
        35                  40                  45

Gly Asp Ile Asn His Ser Gly Thr Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Arg Pro His Tyr Gly Asp Tyr Ser Asp Ala Phe Asp Ile Trp Gly Gln
            100                 105                 110

Gly Thr Met Val Thr Val Ser Ser Ser
        115                 120
```